(12) United States Patent
Takiguchi

(10) Patent No.: US 8,340,755 B2
(45) Date of Patent: Dec. 25, 2012

(54) ELECTRIC FIELD CONTROL DEVICE AND DETECTION DEVICE

(75) Inventor: Kiyoaki Takiguchi, Kanagawa (JP)

(73) Assignee: Sony Corporation, Tokyo (JP)

( * ) Notice: Subject to any disclaimer, the term of this patent is extended or adjusted under 35 U.S.C. 154(b) by 1642 days.

(21) Appl. No.: 11/783,768

(22) Filed: Apr. 12, 2007

(65) Prior Publication Data

US 2007/0244409 A1     Oct. 18, 2007

(30) Foreign Application Priority Data

Apr. 14, 2006   (JP) ............................... P2006-112270

(51) Int. Cl.
*A61B 5/05* (2006.01)
(52) U.S. Cl. ...................................................... 600/547
(58) Field of Classification Search .................... 600/547
See application file for complete search history.

(56) References Cited

U.S. PATENT DOCUMENTS

| | | | | |
|---|---|---|---|---|
| 4,540,002 | A | | 9/1985 | Atlas |
| 5,353,802 | A | * | 10/1994 | Ollmar ........................... 600/547 |
| 5,914,701 | A | * | 6/1999 | Gersheneld et al. .......... 345/156 |
| 2006/0077616 | A1 | | 4/2006 | Takiguchi |
| 2007/0055123 | A1 | | 3/2007 | Takiguchi |

FOREIGN PATENT DOCUMENTS

| | | |
|---|---|---|
| DE | 1 126 559 | 3/1962 |
| EP | 1 658 809 A1 | 5/2006 |
| JP | 59-148855 | 8/1984 |
| JP | T 06-502323 | 3/1994 |
| JP | 2005073974 * | 8/2003 |
| JP | 2004-261243 | 9/2004 |
| JP | 2004-282733 | 10/2004 |
| JP | 2005-073974 | 3/2005 |
| JP | 2005-73974 | 3/2005 |
| JP | 2007-159736 | 6/2007 |

OTHER PUBLICATIONS

European Search Report dated Apr. 20, 2010, in EP 07 00 7097.

* cited by examiner

*Primary Examiner* — Max Hindenburg
*Assistant Examiner* — Renee Danega
(74) *Attorney, Agent, or Firm* — Finnegan, Henderson, Farabow, Garrett & Dunner LLP

(57) ABSTRACT

The present invention provides an electric field control device that can transmit a quasi-electrostatic field more efficiently. There is provided an electric field control device that applies electric fields to an electric field application subject, which includes a first electrode and a second electrode that generate the electric fields, a frame that is arranged around the first electrode and second electrode, and is connected to the first electrode and second electrode, an opening that is formed at one end of the frame, and an output unit that outputs a first signal to the first electrode, and outputs a second signal to the second electrode, wherein, when the electric fields are generated from the first electrode and second electrode, the output unit outputs the second signal to the second electrode so that the potential of the frame is not changed temporally and made constant.

17 Claims, 20 Drawing Sheets

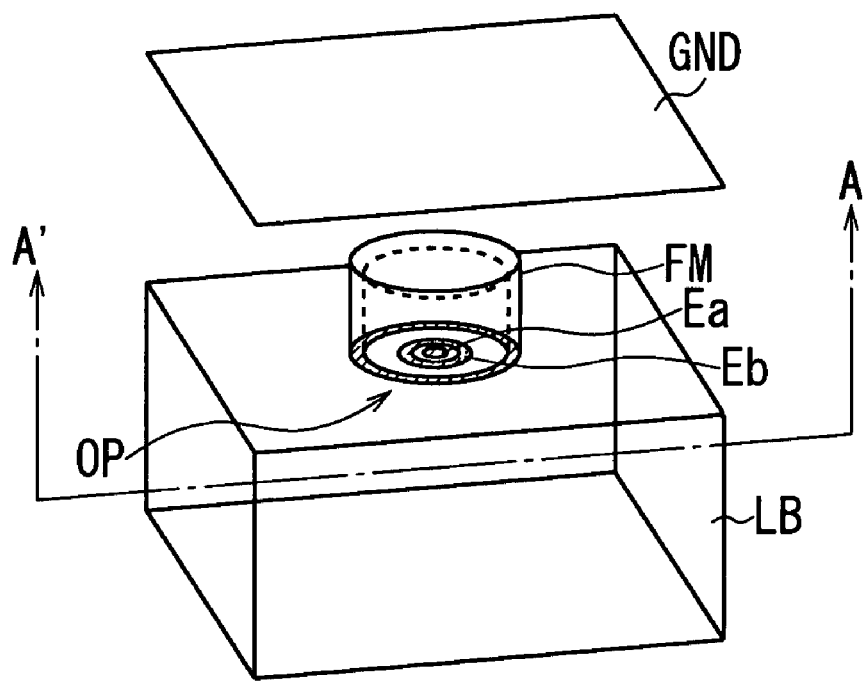
FIG. 7A
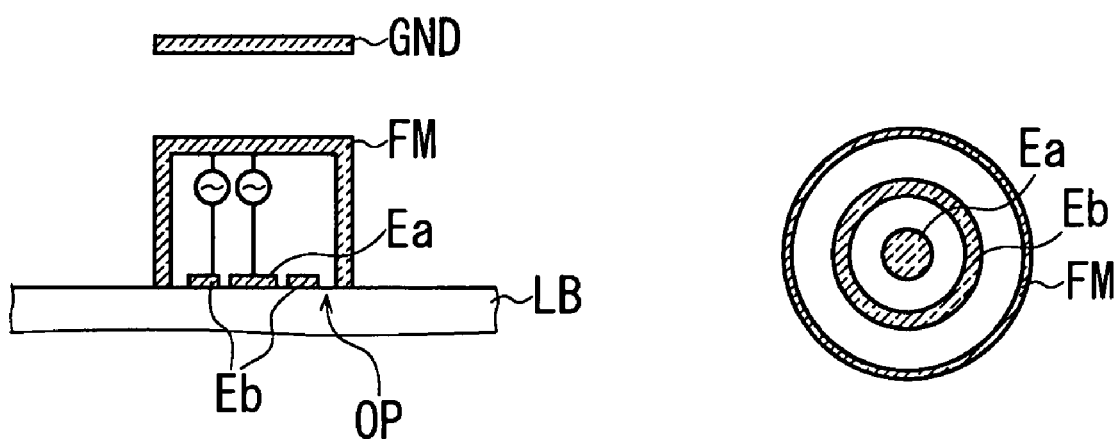
FIG. 7B
FIG. 7C

| Potential of electrode Eb [V] | Electric field intensity between conductive frame and ground [dBV/m] | View indicative of electric field intensity distribution pattern |
|---|---|---|
| 0.1 | 9.2321 | — |
| 0.12 | 6.7960 | FIG. 9 |
| 0.14 | 2.5412 | — |
| 0.15 | 2.0680 | FIG. 10 |
| 0.17 | −5.0501 (Minimum) | FIG. 11 |
| 0.2 | 2.6801 | FIG. 12 |
| 0.25 | 7.9769 | — |
| 0.3 | 12.6770 | — |

FIG. 8

ELECTRIC FIELD CONTROL DEVICE AND DETECTION DEVICE

CROSS REFERENCES TO RELATED APPLICATIONS

The present invention contains subject matter related to Japanese Patent Application JP 2006-112270 filed in the Japanese Patent Office on Apr. 14, 2006, the entire contents of which being incorporated herein by reference.

BACKGROUND OF THE INVENTION

1. Field of the Invention

The present invention relates to an electric field control device and a detection device which may be suitably applied to the case of detecting the state of a blood vessel non-invasively.

2. Description of Related Art

In the past, as a detection device of this type, by paying notice to the fact that the electrical characteristics (relative dielectric constant and electrical conductivity) of the respective tissues in low frequency bands are clearly different from each other, there has already been suggested a detection device that detects the state of a blood vessel non-invasively from above the skin based on the change in impedance in the biomedical tissues by the present applicant (refer to Jpn. Pat. Appln. Laid-Open Publication No. 2005-073974).

Specifically, this detection device detects the impedance of a living organism, which is placed in the quasi-electrostatic fields generated by a plurality of electrodes, from the electrodes respectively, and detects whether or not blood exists in the inside of the living organism based on the detection result.

On the other hand, in this detection device, there are arranged conductive members for dividing off the electrodes respectively, which conductive members are electrically separated from the plural electrodes, and the conductive members are so configured as to narrow down the quasi-electrostatic fields generated by the respective electrodes by means of dividing-off surfaces thereof.

SUMMARY OF THE INVENTION

In thus configured detection device, since the conductive member is merely arranged around the circumference of the electrode, the potential is changed depending on the quasi-electrostatic field transmitted by the electrode. Accordingly, in this detection device, since the quasi-electrostatic field is transmitted to the outside of the conductive member, the transmission efficiency of the quasi-electrostatic field is deteriorated.

It is therefore desirable to overcome the above-mentioned drawbacks by providing an electric field control device that can transmit an electric field more efficiently, and a detection device that can improve the detection accuracy.

According to an embodiment of the present invention, there is provided an electric field control device that applies electric fields to an electric field application subject, including: a first electrode and a second electrode that generate the electric fields; a frame that is arranged around the first electrode and second electrode, and is connected to the first electrode and second electrode; an opening that is formed at one end of the frame; and an output means for outputting a first signal to the first electrode, and outputting a second signal to the second electrode; wherein, when the electric fields are generated from the first electrode and second electrode, the output means outputs the second signal to the second electrode so that the potential of the frame is not changed temporally and made constant.

Accordingly, in the electric field control device, since the second electrode comes to be provided with the function of suppressing the oscillation of the frame due to the electric field generated by the first electrode to which the first signal is output, irrespective of the fact that whether or not the frame is grounded, the electric field generated by the first electrode to which the first signal is output and the electric field generated by the second electrode to which the second signal is output negate each other. Accordingly, the electric fields do not leak to the outside of the frame due to the oscillation thereof, and the electric fields are applied to the opening direction of the frame. As a result, in the electric field control device, the influence from the outside of the frame with respect to the electric fields can be reduced, and the electric fields can be narrowed down to the opening direction.

According to an embodiment of the present invention, there is also provided a detection device that detects a predetermined detection subject in a living organism, including: a first electrode and a second electrode; a frame that is arranged around the first electrode and second electrode, and is connected to the first electrode and second electrode; an opening that is formed at one end of the frame; an output means for outputting a first signal and a second signal to the corresponding first electrode and second electrode by setting frequencies thereof so that, in the electric fields formed through the opening by the first electrode and second electrode, the intensity of the quasi-electrostatic fields is superior as compared with that of the induction fields at a predetermined distance; an impedance detection means for detecting the impedance of the living organism placed in the electric fields from the first electrode and second electrode; and a colloid detection means for detecting whether or not a colloid exists in the inside of the living organism according to the difference of the respective detected impedances; wherein, when the electric fields are generated from the first electrode and second electrode, the output means outputs the second signal to the second electrode so that the potential of the frame is not changed temporally and made constant.

Accordingly, in the detection device, since the second electrode comes to be provided with the function of suppressing the oscillation of the frame due to the electric field generated by the first electrode to which the first signal is output, irrespective of the fact that whether or not the frame is grounded, the electric field generated by the first electrode to which the first signal is output and the electric field generated by the second electrode to which the second signal is output negate each other. Accordingly, the electric fields do not leak to the outside of the frame due to the oscillation thereof, and the electric fields are applied to the opening direction of the frame. As a result, in the detection device, the influence from the outside of the frame with respect to the electric fields can be reduced, and the electric fields can be narrowed down to the opening direction, which makes it possible to accurately detect whether or not a colloid exists in the inside of the living organism according to the difference of the impedances.

As has been described above, according to the present invention, the influence from the outside of the frame with respect to the electric fields can be reduced, and the electric fields can be narrowed down to the opening direction, which makes it possible to provide an electric field control device that can generate the electric field more effectively and a detection device that can improve detection accuracy.

The nature, principle and utility of the invention will become more apparent from the following detailed descrip-

BRIEF DESCRIPTION OF THE DRAWINGS

In the accompanying drawings:

FIGS. 7A to 7C show schematic views of a model of the third simulation;

FIG. 8 shows a table indicative of the result of the third simulation;

DETAILED DESCRIPTION OF THE PREFERRED EMBODIMENTS

(1) General Outline of the Method of Detecting the Blood Vessel State

Figure 1:
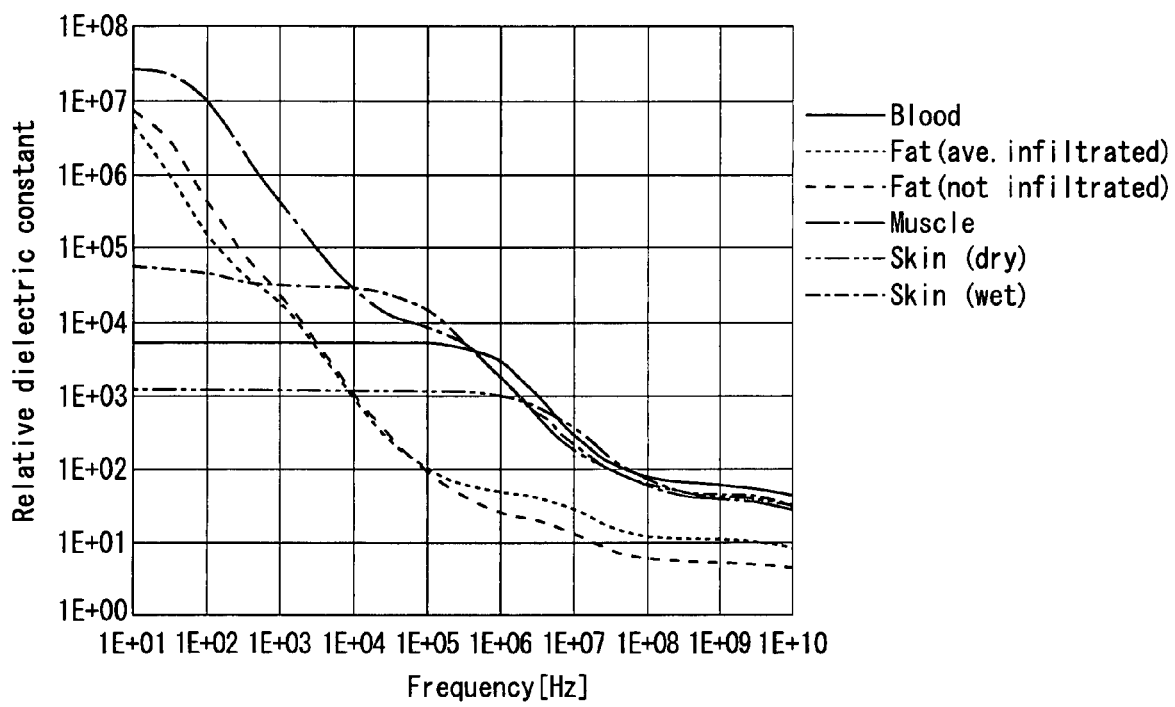
FIG. 1 shows a graphical representation indicative of the relationship between the frequency and relative dielectric constant of respective tissues.
Figure 2:
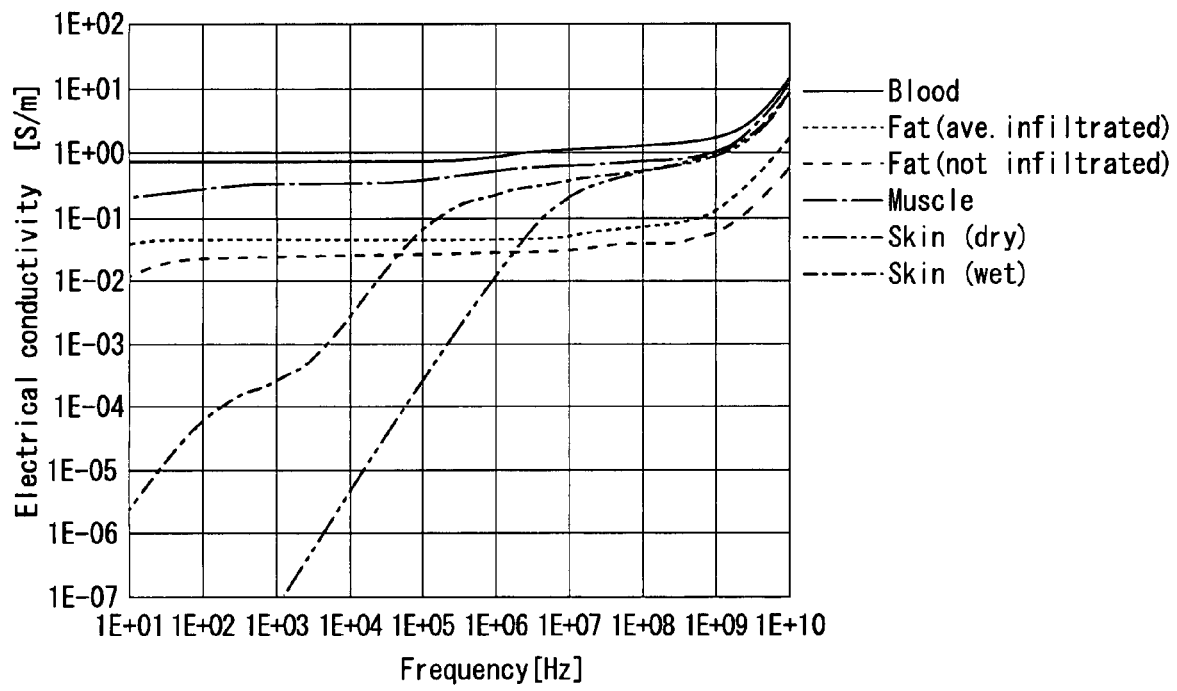
FIG. 2 shows a graphical representation indicative of the relationship between the frequency and electrical conductivity of respective tissues.

FIG. 1 shows a graphical representation indicative of the relationship between the frequency and relative dielectric constant of respective tissues in the inside of a human organism, while FIG. 2 shows a graphical representation indicative of the relationship between the frequency and electrical conductivity. Those frequency, relative dielectric constant, and electrical conductivity are represented by exponents. As is clear from FIG. 1 and FIG. 2, even if the relative dielectric constant and electrical conductivity of the respective tissues are unique, being congested in high frequency bands, it is inconvenient to detect a specific tissue using the high frequency bands.

On the other hand, since the difference between the relative dielectric constants and electrical conductivities of the respective tissues are made large in low frequency bands, it is convenient to detect a specific tissue using the low frequency bands. Especially, since values of blood are clearly different from those of other tissues from approximately 1 MHz to 10 MHz, the blood is convenient as a subject to be detected.

By paying notice to the fact that the electrical characteristics (relative dielectric constant and electrical conductivity) of the respective tissues in low frequency bands are clearly different from each other, in this embodiment, the state of a blood vessel is detected non-invasively from above the skin based on the change in impedance in the biomedical tissues.

Specifically, a signal in a frequency band in which the electrical characteristics of the various biomedical tissues in a living organism are scattered are applied to a plurality of electrodes, and the impedances of the living organism placed in the quasi-electrostatic fields transmitted by the plural respective electrodes are detected from the electrodes respectively.

Since the impedance becomes small when the electrode position comes close to a blood vessel (blood), it is possible to detect under which electrode the blood vessel exists based on the difference in impedances detected by the respective electrodes.

Furthermore, since the impedance becomes small when the electrode position comes close to a blood vessel (blood), it is possible to detect the thickness of the blood vessel and the depth from the surface of the living organism to the blood vessel from an electrode from which the minimum impedance is detected based on the distances to neighboring electrodes and the impedance values detected by the neighboring electrodes.

These items have been disclosed by the present applicant already, and details of which can be referred to "(2) Simulation" written in "DETAILED DESCRIPTION OF THE PREFERRED EMBODIMENTS" of Jpn. Pat. Appln. Laid-Open Publication No. 2005-073974.

(2) Relationship Between the Frequency and the Electric Field

As has been described above, since the electrical conductivities and relative dielectric constants of the respective tissues are scattered in low frequency bands, it is convenient to detect a specific tissue using the low frequency bands. Hereinafter, the relationship between the frequency and the electric field will be explained.

In the electric field, there is generated a composite electric field composed of a radiation field that is inversely proportional to the distance from the electric field source linearly, an induction field that is inversely proportional to the square of the distance from the electric field source, and a quasi-electrostatic field that is inversely proportional to the cube of the distance from the electric field source.

Since the quasi-electrostatic field has a high resolution with respect to the distance, of the electric fields generated from the electric field source, when the intensity of the induction field and the intensity of the radiation field are weakened, it becomes possible to measure the impedances of the biomedical tissues with high accuracy.

Figure 3:
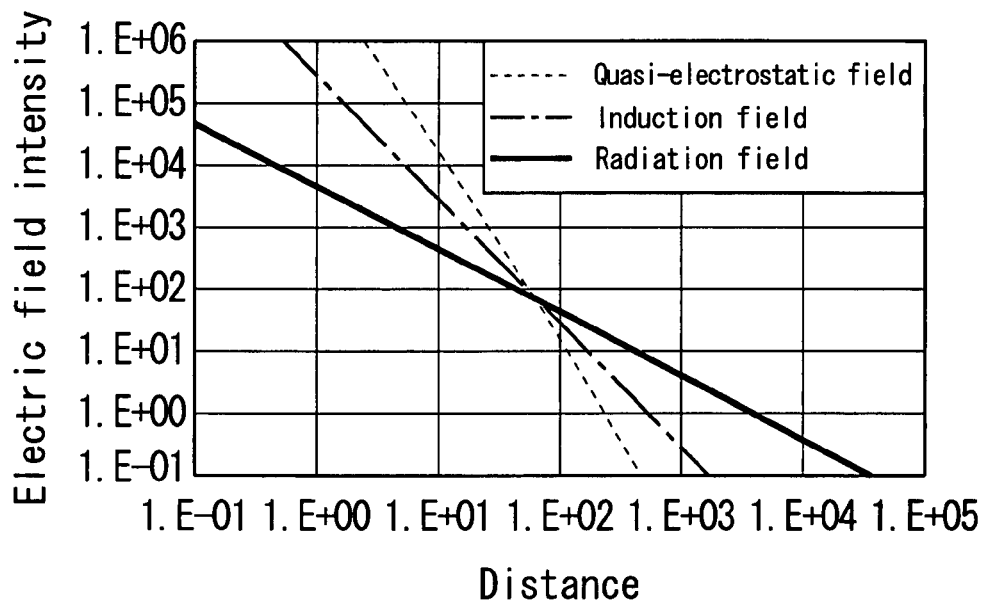
FIG. 3 shows a graphical representation indicative of the relative change of intensity (1 MHz) of respective electric fields depending on the distance.

FIG. 3 shows a graphical representation indicative of the relationship between the relative intensities of the respective radiation field, induction field, quasi-electrostatic field and the distance. In FIG. 3, the relationship between the relative intensities of the respective electric fields and the distance in 1 MHz is represented by exponents.

As is clear from FIG. 3, there exists a distance (referred to as intensity boundary point, hereinafter) at which the relative intensities of the respective radiation field, induction field, and quasi-electrostatic field are equal to each other. In this case, the radiation field is superior (the intensity of the radiation field is larger than those of the induction field and quasi-electrostatic field) in a space which is farther than the intensity boundary point, while the quasi-electrostatic field is superior (the intensity of the quasi-electrostatic field is larger than those of the radiation field and induction field) in a space which is closer than the intensity boundary point.

In case of deriving the Maxwell equations from a point of view of the electric field intensity, the intensity boundary point can be represented by the following mathematical expression, where the distance is "r" m and the wave number is "k" 1/m.
[Formula 1]

$$r = \frac{1}{k} \quad (1)$$

Then, the wave number "k" in the mathematical expression (1) can be represented by the following mathematical expression, where the transmission speed in medium in the electric field is "v" m/s and the frequency is "f" Hz.
[Formula 2]

$$k = \frac{2\pi f}{v} \quad (2)$$

Furthermore, the transmission speed "v" can be represented by the following mathematical expression, where the velocity of light is "c" m/s ($c=3\times10^8$) and the relative dielectric constant of medium is "$\varepsilon$".
[Formula 3]

$$v = \frac{c}{\sqrt{\varepsilon}} \quad (3)$$

Accordingly, the intensity boundary point can be represented by the following mathematical expression that is obtained by inputting the mathematical expressions (2) and (3) into the mathematical expression (1) and arranging the resultant mathematical expression.
[Formula 4]

$$r = \frac{c}{2\pi f \cdot \sqrt{\varepsilon}} \quad (4)$$

As can be seen from the mathematical expression (4) in case of broadening a space in which the intensity of the quasi-electrostatic field is larger than those of the radiation field and induction field (referred to as quasi-electrostatic field superiority space, hereinafter), the frequency is closely related, and the lower the frequency is, the broader the quasi-electrostatic field superiority space becomes. That is, the lower the frequency is, the longer the distance to the intensity boundary point shown in FIG. 3 becomes, more specifically, the intensity boundary point shifts to the right. On the other hand, the higher the frequency is, the narrower the quasi-electrostatic field superiority space becomes. That is, the higher the frequency is, the shorter the distance to the intensity boundary point shown in FIG. 3 becomes, more specifically, the intensity boundary point shifts to the left.

Figure 4:
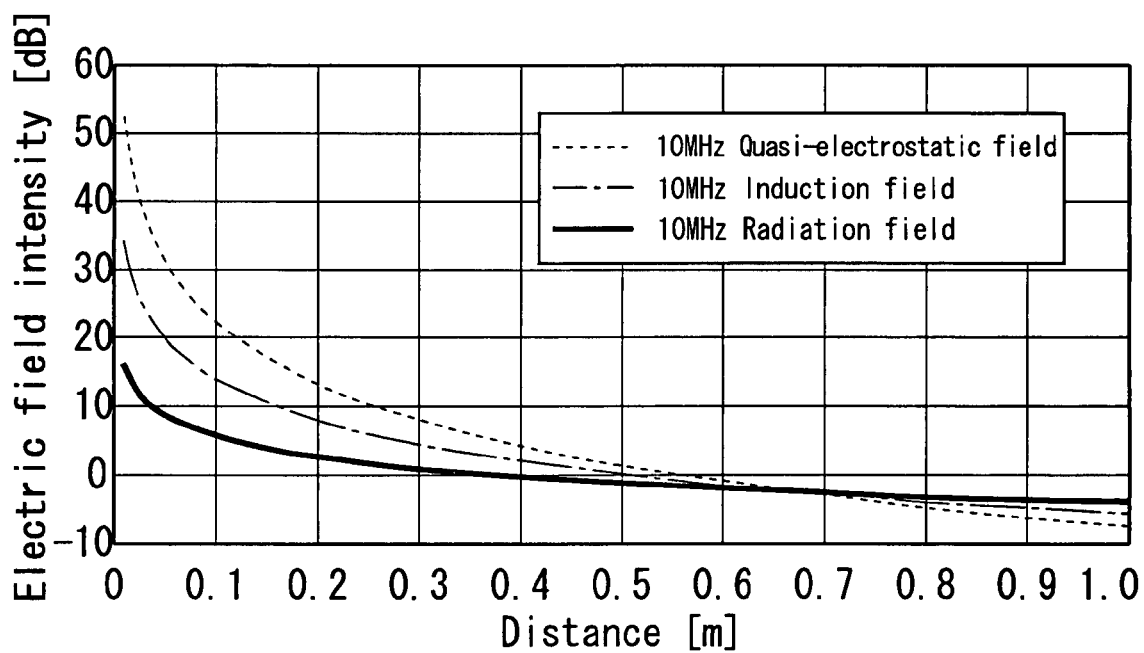
FIG. 4 shows a graphical representation indicative of the relative change of intensity (10 MHz) of respective electric fields depending on the distance.

For example, in case 10 MHz is selected, assuming that the relative dielectric constant of a human organism is evenly 50, it can be seen that the quasi-electrostatic field is superior at a point which is closer than 0.675 m from the mathematical expression (4). FIG. 4 shows a graphical representation indicative of the relationship between the relative intensities of the respective radiation field, induction field, quasi-electrostatic field and the distance in case 10 MHz is selected.

As is clear from FIG. 4, the intensity of the quasi-electrostatic field at 0.01 m point from the electric field source becomes large by 18.2 dB as compared with that of the induction field. Accordingly, it can be considered that the quasi-electrostatic field in this case is not influenced by the induction field and radiation field.

In this way, when a low frequency band is selected, since the intensities of the induction field and radiation field of the electric field generated from the electric field source are weakened, it can be seen that the impedances in the biomedical tissues can be detected with high accuracy. Details can be referred to "(3) Relationship between the frequency and the electric field" written in "DETAILED DESCRIPTION OF THE PREFERRED EMBODIMENTS" of Jpn. Pat. Appln. Laid-Open Publication No. 2005-073974.

As described above, in low frequency bands, not only from the viewpoint of the electrical conductivities and relative dielectric constants of the respective tissues, but also from the viewpoint of the influence by the induction field and radiation field, it is convenient to detect a specific tissue.

(3) Controlling the Directivity of the Quasi-Electrostatic Field

It has been described that a signal of a low frequency band is applied to electrodes arranged at the surface of a living organism, and a specific tissue (especially, a blood vessel) can be detected based on the impedances of the living organism placed in the quasi-electrostatic fields transmitted by the electrodes.

On the other hand, since the quasi-electrostatic field spreads to the surrounding area from the electrode, the mutual interaction result of the quasi-electrostatic field that is not emitted on the living organism and fluctuating elements other than the living organism influences the impedance of the living organism placed in the quasi-electrostatic field, which may not attain the purpose of improving the detection accuracy.

In order to suppress the quasi-electrostatic field that is not emitted on the living organism, there may be employed a method of arranging a frame made of conductive material (referred to as conductive frame, hereinafter) to enclose the electrode in all directions excluding the irradiation direction (or direction facing the surface of the living organism), and grounding the conductive frame.

Under this method, since the electric charge in the conductive frame is so collected, to the surface thereof, as to negate the quasi-electrostatic field generated by the electrode, the quasi-electrostatic field that is not emitted on the living organism can be suppressed, and the quasi-electrostatic field spreads only in the irradiation direction (or direction facing the surface of the living organism). As a result, fluctuating elements other than the living organism do not influence the impedance of the living organism placed in the quasi-electrostatic field.

Figure 5:
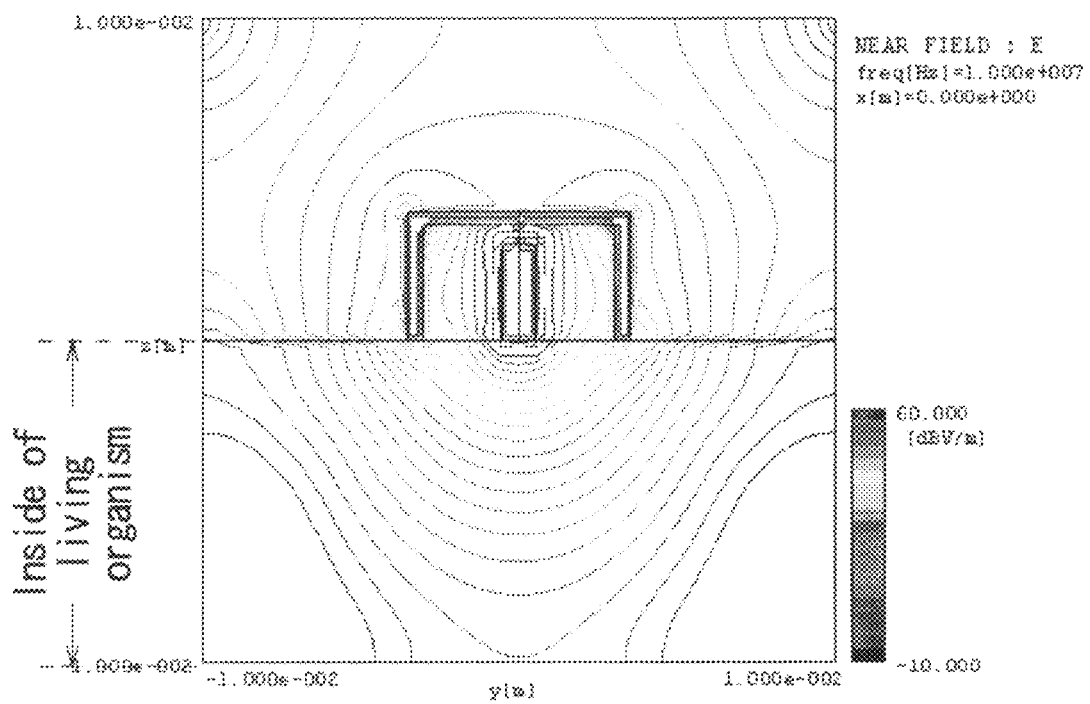
FIG. 5 shows a view indicative of an electric field intensity distribution pattern by the first simulation.

This method is restricted to the case under the condition in which the conductive frame is electrically grounded through a conductor, and free electrons shift to the ground and are set to "0" at any time, that is, the conductive frame is sufficiently grounded. In case of mounting to a portable device, in which case the grounding is unstable or the grounding is not carried out sufficiently, when the simulation is performed (referred to as first simulation, hereinafter), an electric field distribution pattern shown in FIG. 5 can be obtained. The electric field distribution pattern shown in FIG. 5 is appended as a reference FIG. 1.

In this first simulation model, a cylindrical electrode with the radius 0.5 mm is employed, and, as the conductive frame enclosing the electrode, a cylindrical conductive frame in the form of a concavity in its cross-section with the inside diameter 1.0 mm and outside diameter 1.5 mm is employed. The conductive frame is not grounded, that is electrically floating, and a signal of 10 MHz in frequency is applied to the electrode. Furthermore, the electrical characteristics in the living organism are set equal with those of the muscle (relative dielectric constant 170 and electrical conductivity 0.6 S/m).

As is clear from the electric field distribution pattern by the first simulation, in case the grounding is not carried out, the quasi-electrostatic field undesirably spreads to the outside of the conductive frame. The reason is that there is undesirably raised a potential difference between the electrode and the conductive frame.

Figure 6:
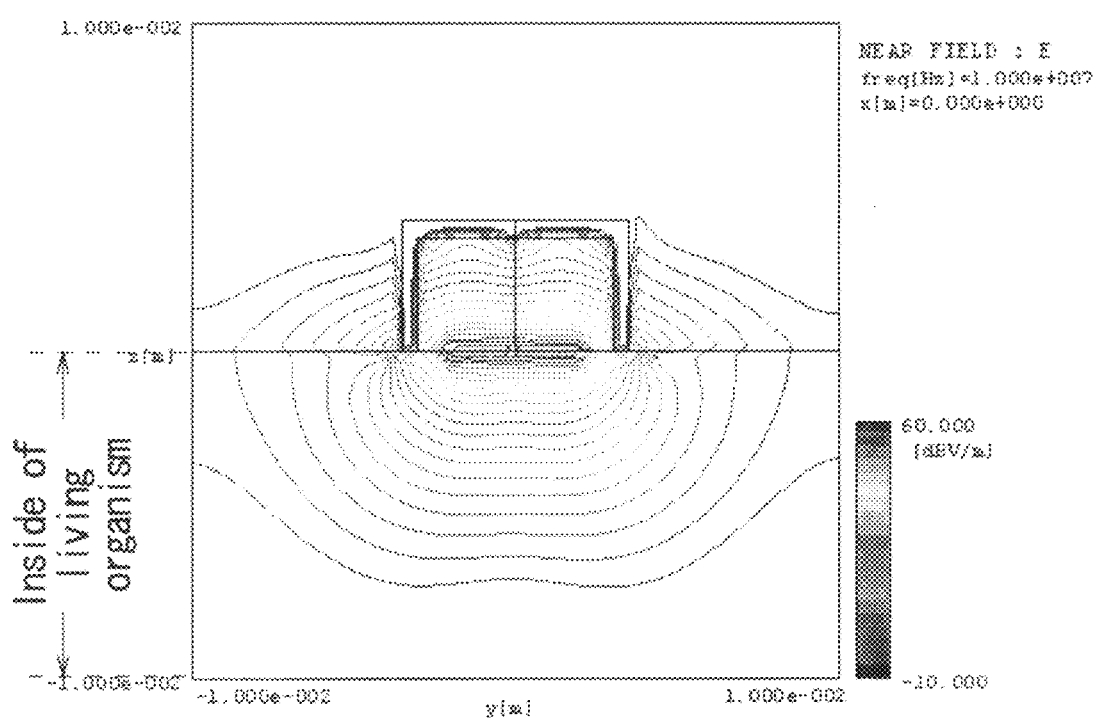
FIG. 6 shows a view indicative of an electric field intensity distribution pattern by the second simulation.
Figure 9:
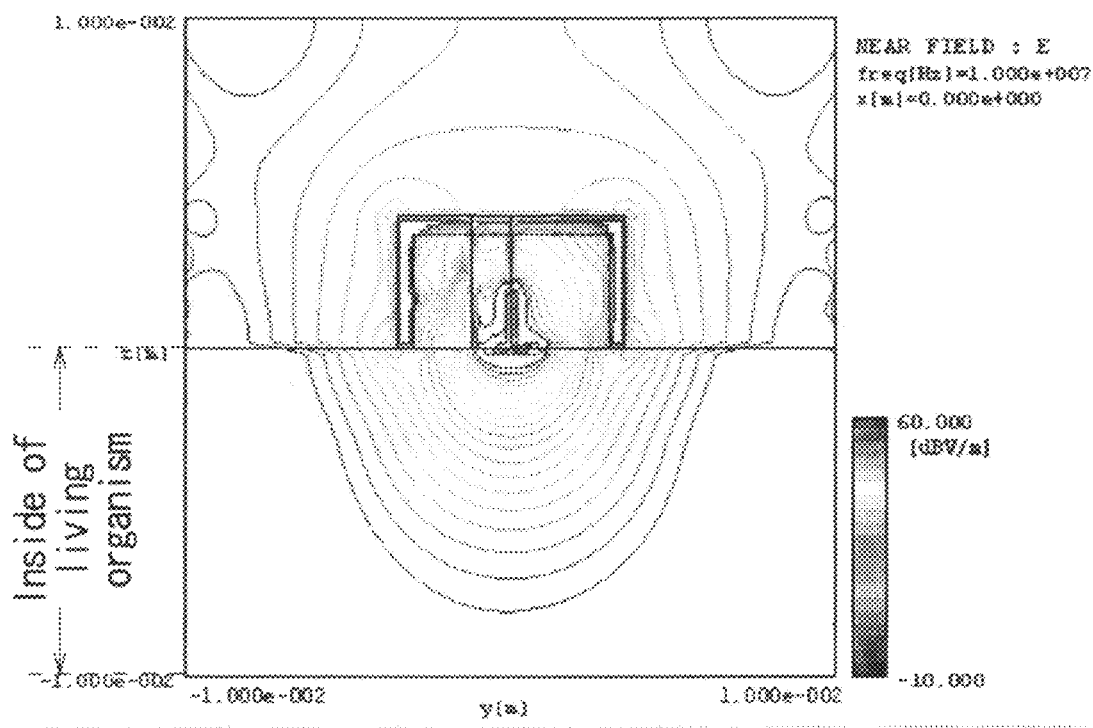
FIG. 9 shows a view indicative of an electric field intensity distribution pattern by the third simulation.
Figure 10:
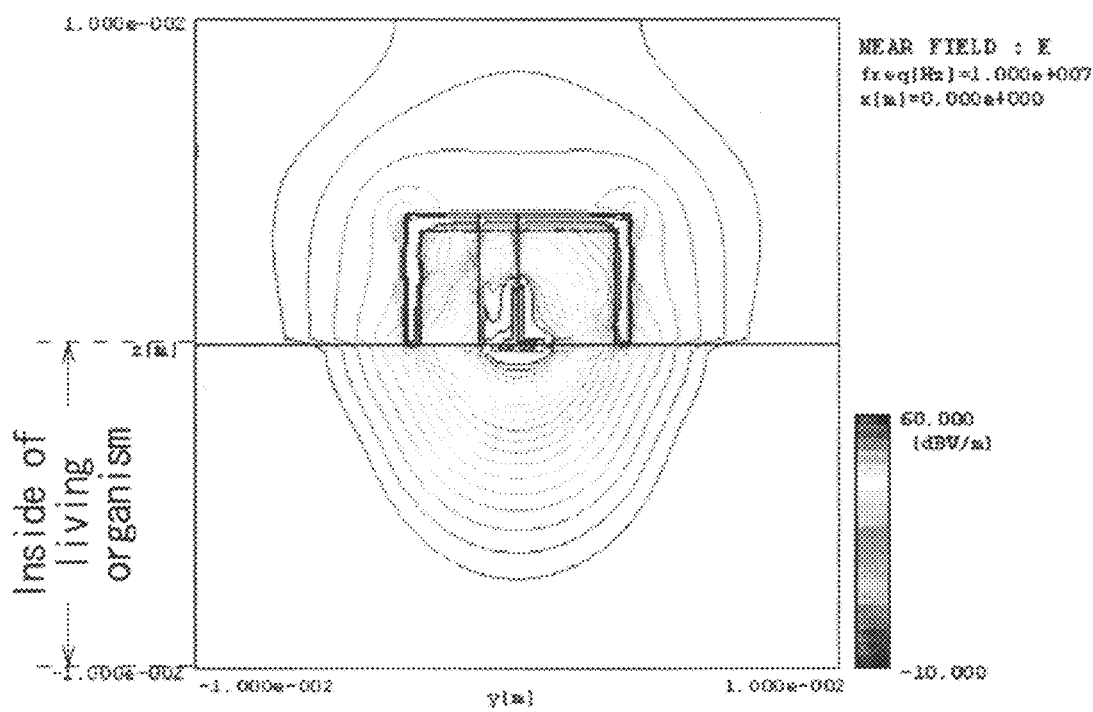
FIG. 10 shows a view indicative of an electric field intensity distribution pattern by the third simulation.

On the other hand, instead of the cylindrical electrode employed in the first simulation model, when a pair of disciform electrodes (dipole) with the radius 0.5 mm are employed, when the simulation is performed (referred to as second simulation, hereinafter), an electric field distribution pattern shown in FIG. 6 can be obtained. The electric field distribution pattern shown in FIG. 6 is appended as a reference FIG. 2.

As is clear from the electric field distribution pattern by the second simulation, the quasi-electrostatic fields generated from the paired electrodes (dipole) scarcely spread to the outside of the conductive frame since phases thereof are opposite to each other, mutually negating each other.

On the other hand, of sides of the paired electrodes (dipole), at portions in closest proximity to the inner wall of the conductive frame, since there is raised a potential difference between the electrode and the conductive frame, the quasi-electrostatic fields spread around the vicinity of the surface of the living organism in the normal line directions of the paired electrodes (dipole), and thus, the impedance of the living organism is unable to be detected in the limited downward direction under the electrodes.

Then, in order to prevent the potential change in the conductive frame (that is, in order to set the potential constant), it is considered that the directivity of the quasi-electrostatic fields can be controlled to the limited downward direction under the electrodes when independent signals are applied to the paired electrodes respectively, and the simulation is performed for this case (referred to as third simulation, hereinafter).

In this third simulation model, as shown in FIGS. 7A to 7C, there are employed a disciform electrode Ea, a ringlike electrode Eb that has its center made to accord with the electrode Ea and symmetrically encloses the electrode Ea, and a conductive frame FM that symmetrically encloses the entire circumference of the electrodes Ea and Eb with the electrode Ea being the center excluding an opening OP being the electric field irradiation part. In this third simulation model, the electrodes Ea and Eb are arranged on the same plane, and are so placed as to be in contact with the surface of the opening OP of the conductive frame FM.

There are employed the electrode Ea with the radius 0.5 mm, electrode Eb with the inside diameter 1.0 mm and outside diameter 1.5 mm, and conductive frame FM with the inside diameter 3.0 mm and outside diameter 3.5 mm, which are electrically floating. Furthermore, the electrical characteristics in a living organism LB is set equal with those of the 10 MHz muscle (relative dielectric constant 170 and electrical conductivity 0.6 S/m).

The signal to be applied to the electrode Ea has its frequency set to 10 MHz and has its amplitude set to 1 V, while the signal to be applied to the electrode Eb has its frequency set to 10 MHz whose phase is shifted by 180° as compared with that of the signal to be applied to the electrode Ea and has its amplitude set variable arbitrarily. Then, the electric field intensity between the conductive frame FM and a ground plate GND that corresponds to the potential of the ground is detected. In case the electric field intensity is sufficiently small, it is considered that there is no potential change in the conductive frame FM and the potential is constant.

FIG. 8 shows a table indicative of the result of the third simulation. FIG. 9 to FIG. 12 shows electric field distribution patterns which are parts of the simulation result. The electric field distribution patterns shown in FIG. 9 to FIG. 12 are appended as reference FIG. 3 to reference FIG. 6.

As is clear from FIG. 8 to FIG. 12, in this third simulation, when the amplitude of the signal to be applied to the core electrode Ea is 1 V, and the amplitude of the signal to be applied to the electrode Eb enclosing the core electrode Ea is 0.17 V, the quasi-electrostatic fields do not spread not only to the outside of the conductive frame FM but also around the vicinity of the surface of the living organism. As a result, the impedance of the living organism can be detected in the limited downward direction under the electrodes.

On the other hand, the amplitude ratio of the signals to be applied to the electrodes Ea and Eb is changed depending on the electrode shape, electrode arrangement state, and conductive frame shape. Accordingly, actually, in the state in which the paired electrodes and conductive frame are built up, the amplitude ratio of the signals to be applied to the paired electrodes is determined such that the electric field intensity is made small at portions of the conductive frame where the electrodes are in closest proximity to the inner wall thereof.

In this way, when independent signals are applied to the paired electrodes respectively such that the potential of the conductive frame is set constant, the directivity of the quasi-electrostatic fields can be controlled in the limited downward direction under the electrodes. As a result, irrespective of the grounding environment, since the impedance of the living organism can be detected in the limited downward direction under the electrodes, it becomes possible to not only realize a detection device that can improve the detection accuracy but also arrange a detection device without taking the grounding state into consideration, which is very convenient.

In above-described simulations, the multipurpose electromagnetic wave analysis software "EEM-FDM" produced by Information and Mathematical Science Laboratory Inc. is employed. This is a software that discretizes the Maxwell equations with the difference method with respect to a specified frequency, and calculates the electric field, magnetic field, and impedance between feeding electrodes in a space.

(4) Embodiments (4-1) Entire Configuration of the Detection Device

Figure 13:
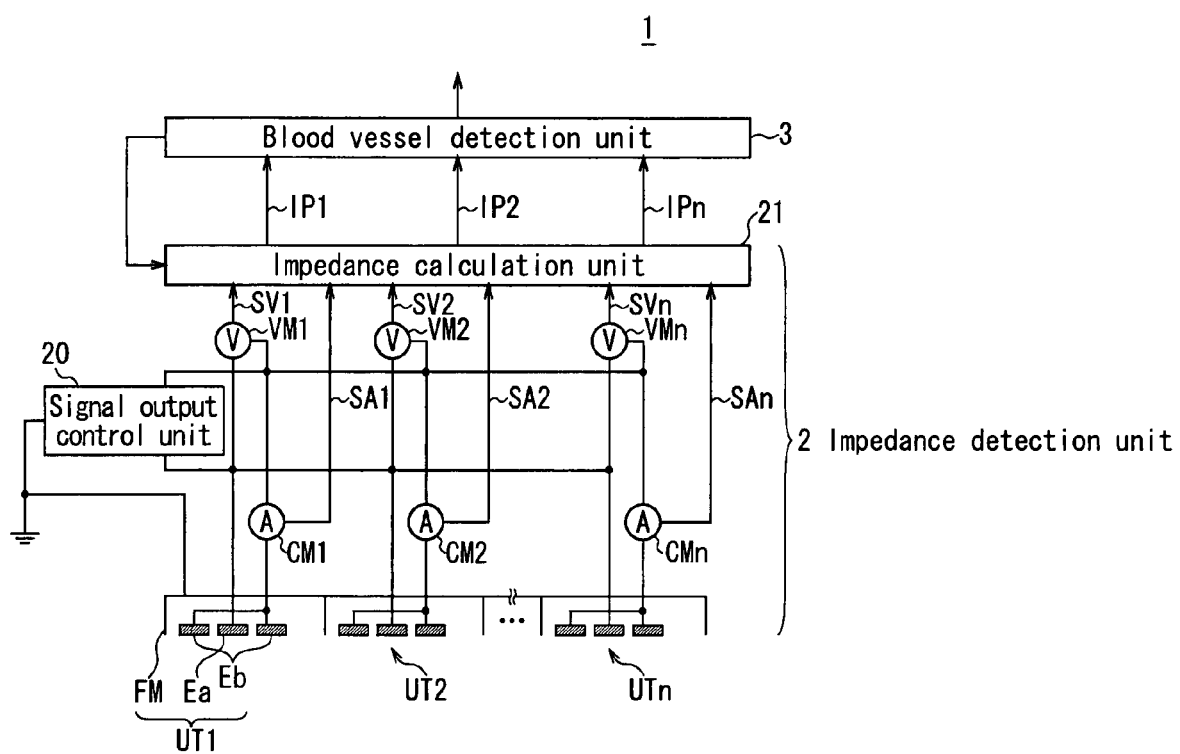
FIG. 13 shows a block diagram indicative of the configuration of a detection device according to an embodiment of the present invention.

FIG. 13 shows a block diagram indicative of the configuration of an embodiment of a detection device 1 that detects a specific tissue using the impedances of the biomedical tissues. The detection device 1 includes an impedance detection unit 2 and a blood vessel detection unit 3.

(4-2) Configuration of the Impedance Detection Unit

The impedance detection unit 2 includes a plurality of electrode units UT1 to UTn which are to abut on a detection subject of a living organism. Each of these electrode units UT1 to UTn includes the paired electrodes Ea, Eb, and conductive frame FM shown in FIGS. 7A to 7C.

That is, each of these electrode units UT1 to UTn includes the disciform electrode Ea, the ringlike electrode Eb that has its center made to accord with the electrode Ea and symmetrically encloses the electrode Ea, and the conductive frame FM that symmetrically encloses the entire circumference of the electrodes Ea and Eb with the electrode Ea being the center excluding the opening OP being the electric field irradiation part. The electrodes Ea and Eb are arranged on the same plane, and are so placed as to be in contact with the surface of the opening OP of the conductive frame FM. The sizes of the electrodes Ea, Eb, and conductive frame FM of the electrode units UT are not restricted to those described using FIGS. 7A to 7C, and are arbitrarily selected.

Furthermore, these electrode units UT1 to UTn are arranged in a lattice-shaped pattern with the surfaces of the openings OP of the conductive frames FM placed on the same plane, and are unitedly formed with the neighboring conductive frames FM coupled with each other, which conductive frames FM are grounded. In FIG. 13, for the sake of convenience, the state in which the electrode units UT1 to UTn are arranged in a line is shown.

As the material of the conductive frame FM, a material having the flexibility is selected. Accordingly, even if these electrode units UT1 to UTn are unitedly formed, the electrodes Ea and Eb thereof which are so placed as to be in contact with the surfaces of the openings OP of the respective conductive frames FM can be attached firmly to the uneven surface of the living organism.

Furthermore, to the paired electrodes Ea, Eb of the electrode units UT1 to UTn, a signal that has its frequency set to, for example, 10 MHz is sent from a signal output control unit 20. This signal is selected with an index concerning under which low frequency band or lower frequency bands the electrical conductivity and relative dielectric constant of a biomedical tissue to be detected can be clearly differentiated from those of other tissues, or approximately which depth a biomedical tissue to be detected exists from the surface of the living organism.

Accordingly, when the paired electrodes Ea, Eb of the electrode units UT1 to UTn are made to abut on the living organism, and a signal is sent to the electrodes Ea, Eb from the signal output control unit 20, according to the signal, the quasi-electrostatic fields generated from the electrodes Ea, Eb come to be emitted on the living organism in the superior state (the intensity of the quasi-electrostatic fields are larger than those of the radiation fields and induction fields) in a space in close proximity to the electrodes (space to the distance corresponding to the selected frequency).

In this case, to an impedance calculation unit 21 of the impedance detection unit 2, measurement results SA1 to SAn by amperemeters CM1 to CMn which are arranged between a signal generation source 25 and the respective electrode units UT1 to UTn are supplied through corresponding switches SW1 to SWn, and a measurement result SV by a voltmeter VM corresponding to the signal generation source 25 is also supplied.

The impedance calculation unit 21 calculates impedance values corresponding to the respective electrode units UT1 to UTn, using the ratio of the measurement result SA1 by the amperemeter CM1 and the measurement result SV by the voltmeter VM, ratio of the measurement result SA2 by the amperemeter CM2 and the measurement result SV by the voltmeter VM, . . . , and ratio of the measurement result SAn by the amperemeter CMn and the measurement result SV by the voltmeter VM. Thus calculated impedance values are represented in the form of complex numbers. In detecting the living organism, it is desirable to employ a component of high sensitivity from among the real component, imaginary component, and combination of these components.

Then, the impedance calculation unit 21 outputs thus obtained impedance values corresponding to the respective electrode units UT1 to UTn to the blood vessel detection unit 3 as data (referred to as impedance data, hereinafter) IP1 to IPn.

Accordingly, the impedance detection unit 2 can detect the impedances of the biomedical tissues.

(4-3) Configuration of the Signal Output Control Unit

Figure 14:
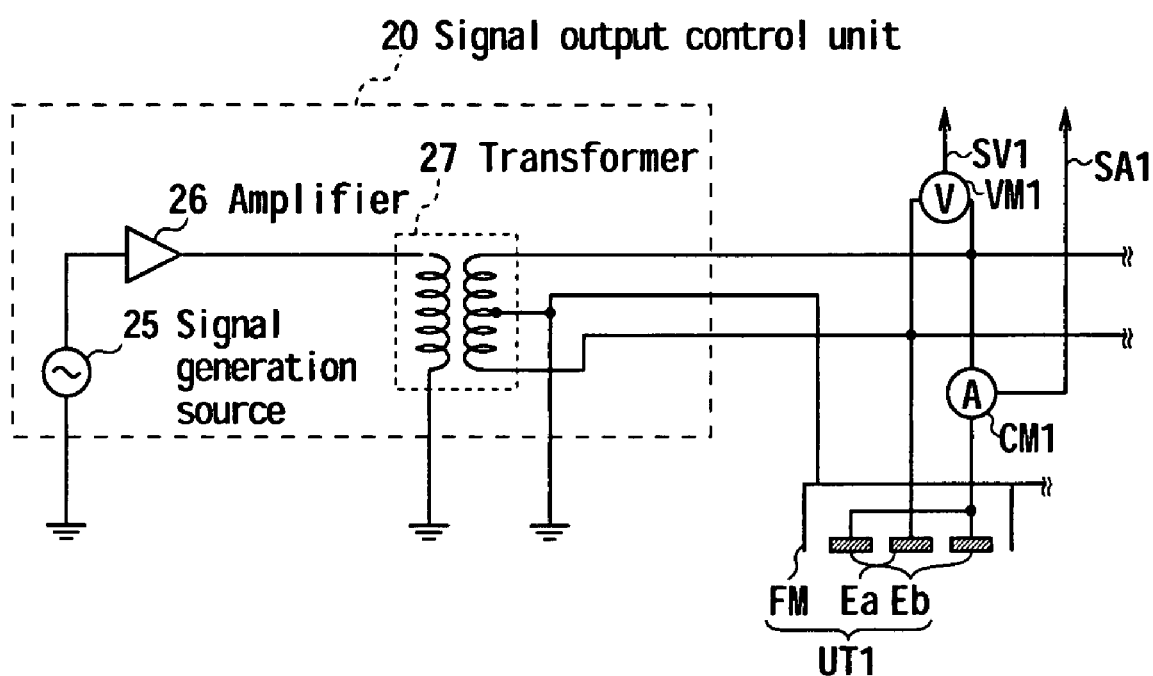
FIG. 14 shows a schematic view indicative of the configuration of a signal output control unit.

FIG. 14 shows a schematic view indicative of the configuration of the signal output control unit 20 of the impedance detection unit 2.

The signal output control unit 20 includes the signal generation source 25, an amplifier 26, and a transformer 27, and a sinusoidal signal of 10 MHz transmitted from the signal generation source 25 is amplified by the amplifier 26, and thus amplified signal is output to the primary coil of the transformer 27.

One end of the secondary coil of the transformer 27 is connected to the electrodes Ea of the respective electrode units UT (UT1 to UTn), while the other end of the secondary coil is connected to the electrodes Eb of the respective electrode units UT.

Furthermore, the secondary coil of the transformer 27 has arranged thereon a plurality of taps, not shown, at predetermined winding intervals, and one tap thereof is connected to the ground for the conductive frames FM of the respective electrode units UT.

As described above, in the state in which the electrode units UTl to UTn are built up, this one tap sets the electric field intensity minimum at portions of the conductive frames FM of the electrode units UT where the electrodes Eb are in closest proximity to the inner wall thereof.

The signal that is transformed by the transformer 27 is output as a signal that has its phase changed by 180° and is of a predetermined amplitude ratio. This amplitude ratio is arbitrarily changed depending on the configuration of the electrode units UT such as the relationship among the clearance between the electrodes Ea and the electrodes Eb and the clearance between the electrodes Eb and the conductive frames FM, and the shape of the electrodes Ea, Eb, and conductive frames FM.

Accordingly, when the signal transformed by the transformer 27 is applied to the paired electrodes Ea and Eb of the respective electrode units UT, the quasi-electrostatic fields generated from the core electrodes Ea and the quasi-electrostatic fields generated from the electrodes Eb enclosing the core electrodes Ea negate each other before getting to the conductive frames FM of the electrode units UT, suppressing the fluctuation of the potential of the conductive frames FM.

Figure 11:
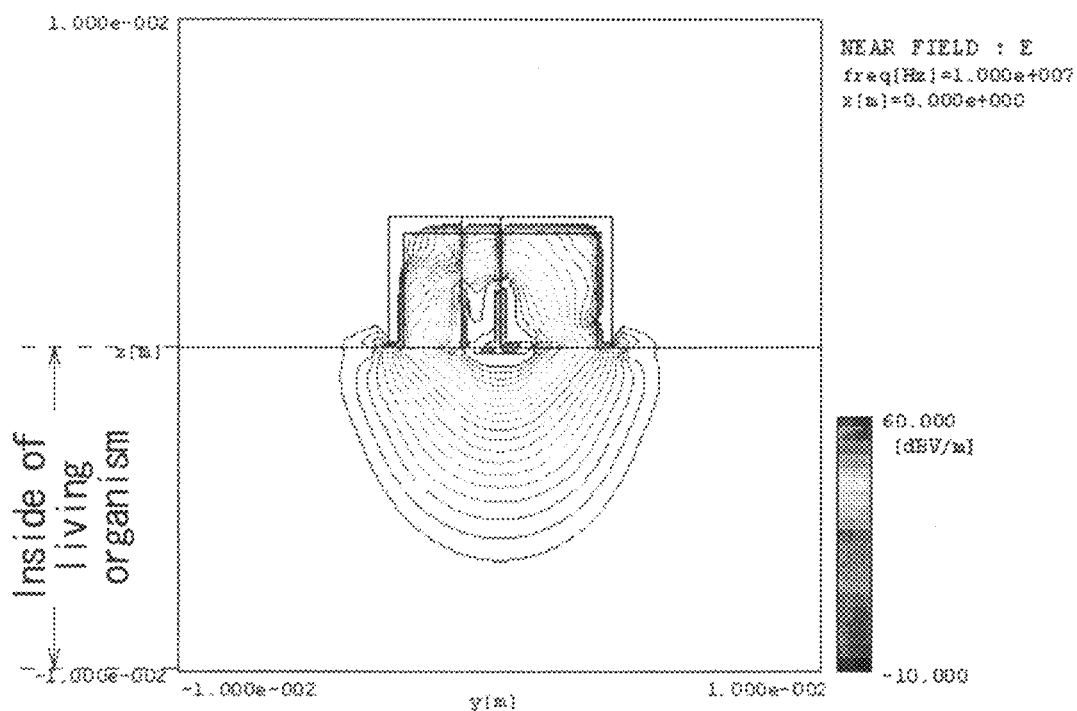
FIG. 11 shows a view indicative of an electric field intensity distribution pattern by the third simulation.
Figure 12:
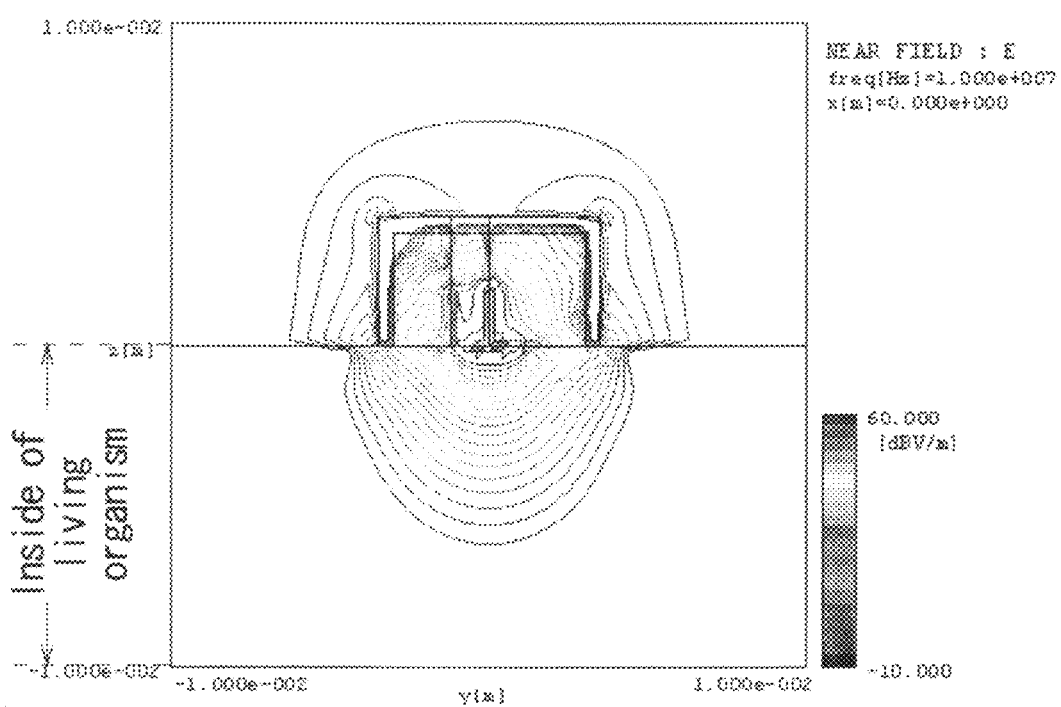
FIG. 12 shows a view indicative of an electric field intensity distribution pattern by the third simulation.

As a result, as shown in FIG. 11, the quasi-electrostatic fields generated from the respective electrode units UT are irradiated to the living organism in the limited downward direction under the paired electrodes Ea and Eb.

Accordingly, the signal output control unit 20 is so configured as to emit the quasi-electrostatic fields in the limited downward direction under the paired electrodes Ea and Eb of the electrode units UT.

(4-4) Configuration of the Blood Vessel Detection Unit

Figure 15:
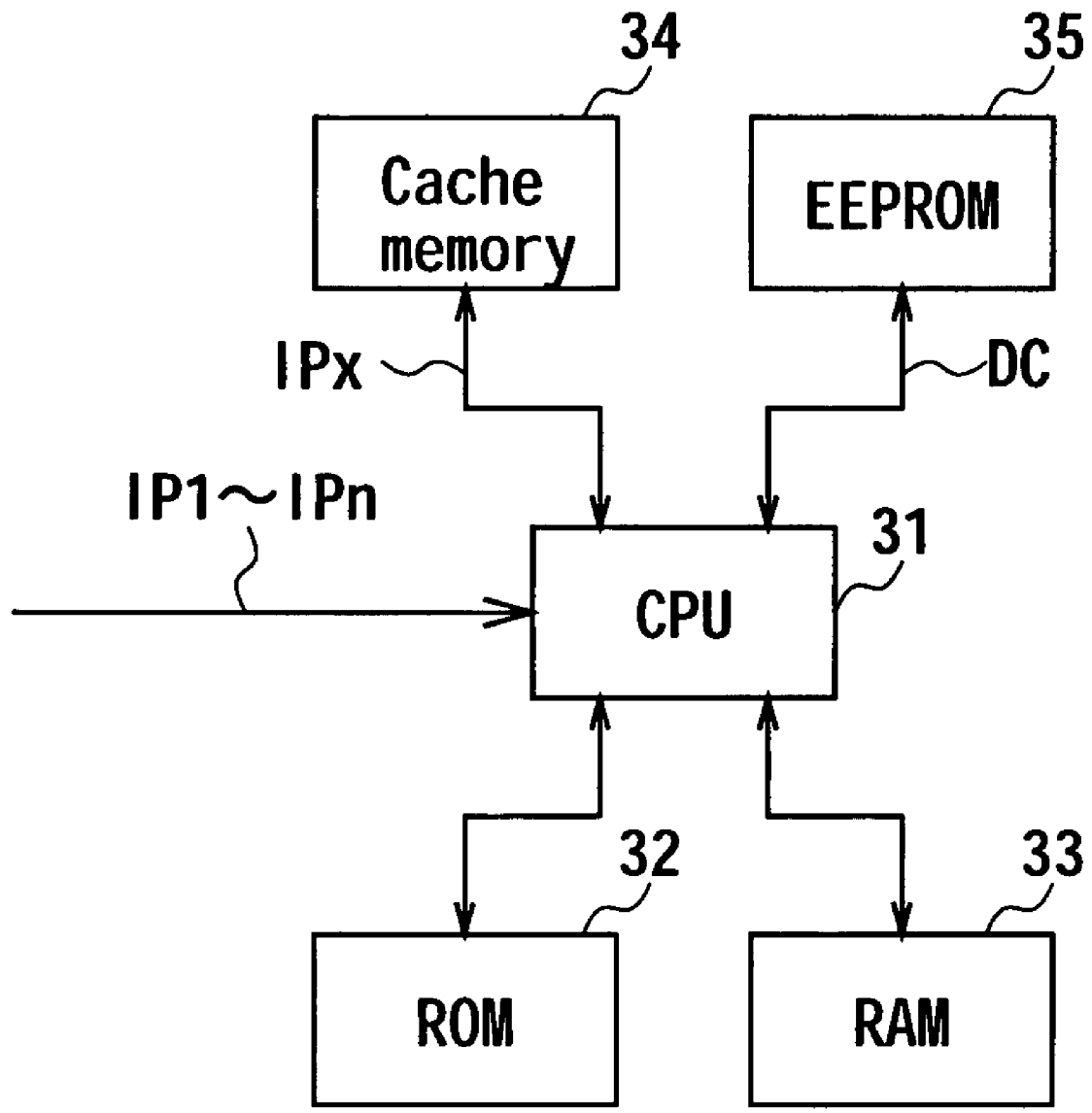
FIG. 15 shows a block diagram indicative of the configuration of a blood vessel detection unit.

On the other hand, as shown in FIG. 15, the blood vessel detection unit 3 includes a Central Processing Unit (CPU) 31, and further a Read Only Memory (ROM) 32 that stores predetermined programs, a Random Access Memory (RAM) 33 that works as a work memory for the CPU 31, a cache memory 34, and an Electrically Erasable Programmable ROM (EEPROM) 35, which are mutually connected to the CPU 31.

The CPU 31 carries out the blood vessel detection processing by arbitrarily controlling the cache memory 34, EEPROM 35, and impedance detection unit 2 shown in FIG. 13 in accordance with the programs stored in the ROM 32.

That is, the CPU 31 controls to switch the electrode units UT to which the signal output from the signal generation source 25 shown in FIG. 14 is sent so that the signal can be sequentially supplied to the respective electrode units UT.

Accordingly, as compared with the case of concurrently applying the signal output from the signal generation source 25 to all the electrode units UT1 to UTn respectively, the CPU 31 can prevent the impedance detection unit 2 from detecting the impedances due to the mutual interaction among quasi-electrostatic fields generated from the neighboring electrodes beforehand.

Figure 16:
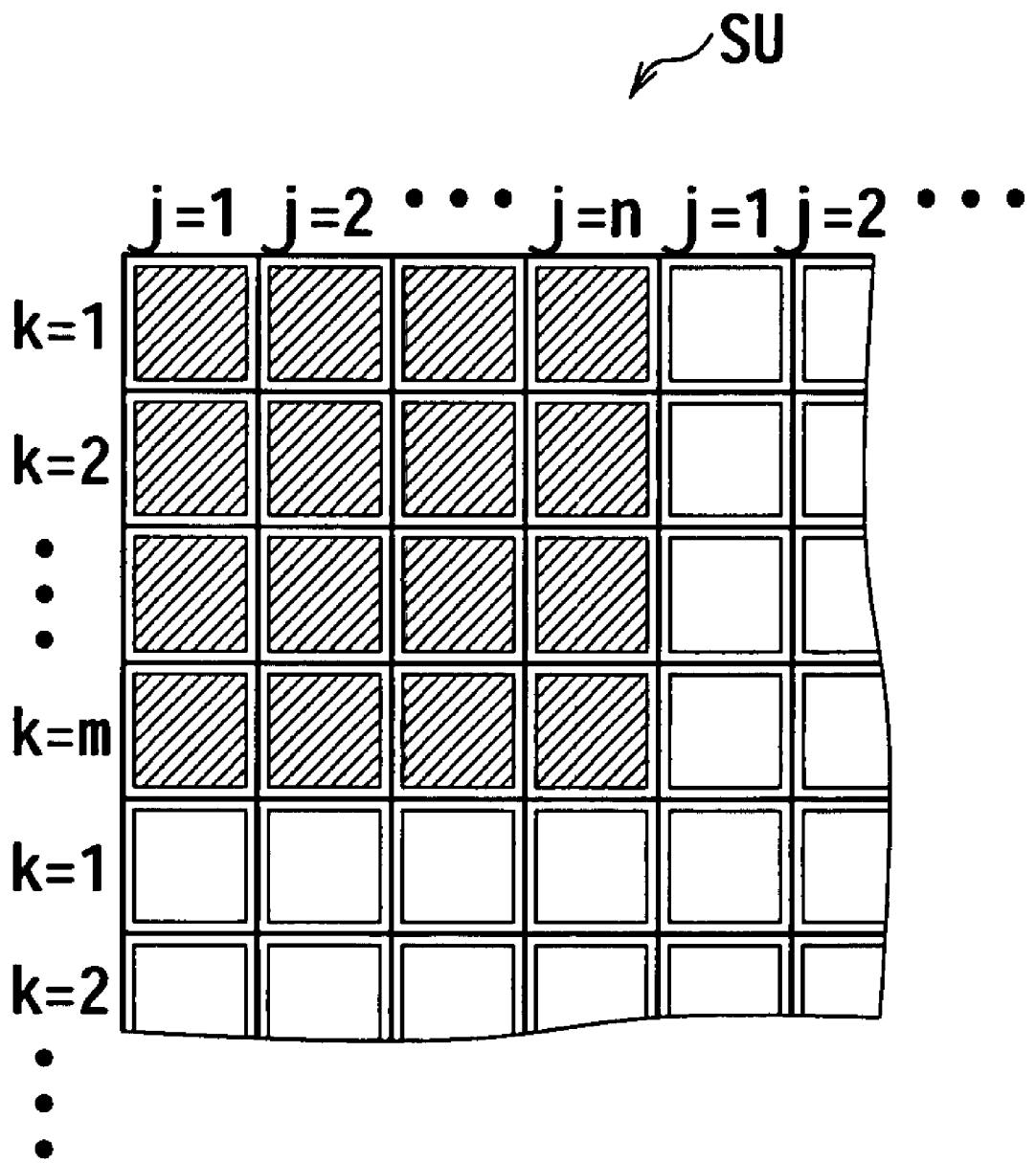
FIG. 16 shows a view for explaining a unit to detect the impedance.

Then, the CPU 31 stores the impedance data IP1 to IPn sequentially supplied from the impedance calculation unit 21 in the cache memory 34, and processes thus stored impedance data IP1 to IPn with electrodes (referred to as unit electrode group, hereinafter) SU of m-row and n-column being a unit, as shown in FIG. 16.

Figure 17:
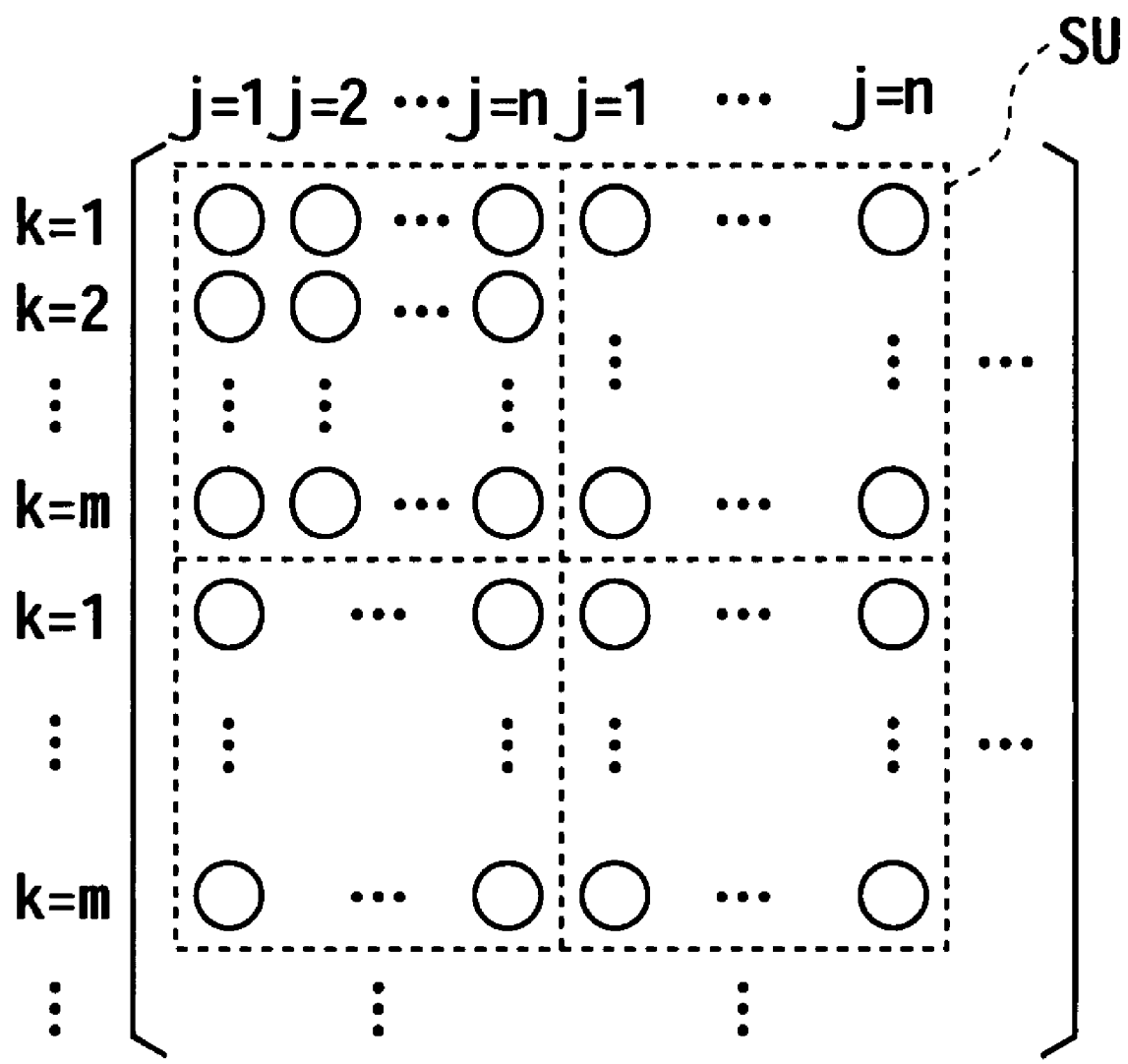
FIG. 17 shows a view for explaining the replacement to a matrix.

Specifically, as shown in FIG. 17, values of the impedance data IP1 to IPn are replaced to a matrix corresponding to the arrangement of the electrodes, and, based on the matrix, the minimum impedance is detected for each unit electrode group SU. As described above, since the impedance becomes small as the electrode arrangement position comes close to blood, the minimum impedance position (ko, jo) represents the center of cross-section surface of a blood vessel in the blood flow direction.

Figure 18:
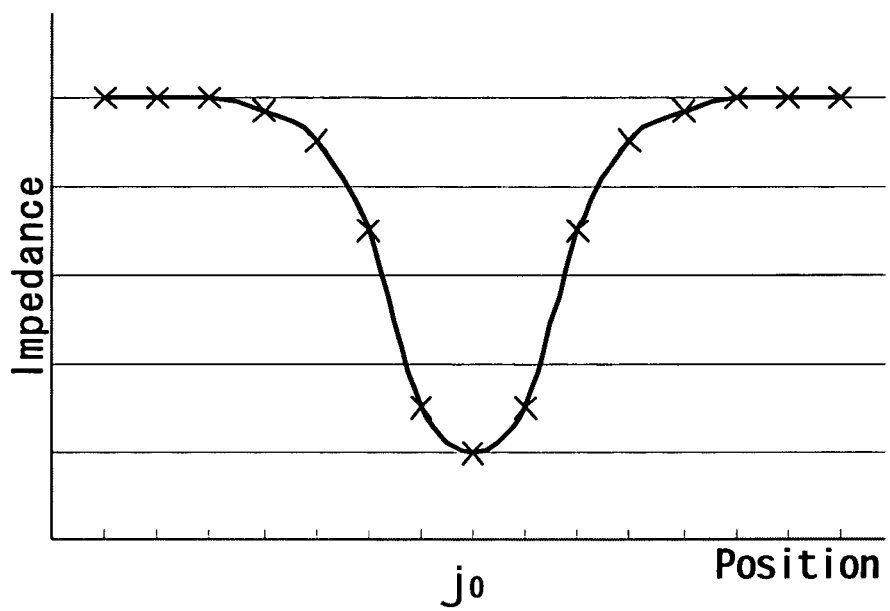
FIG. 18 shows a graphical representation indicative of the relationship between the distance from the minimum impedance position and the impedance value at the distance.

When the minimum impedance position (ko, jo) is detected, as shown in FIG. 18, based on the distance from the minimum impedance position (ko, jo) and the impedance value at the distance, the CPU 31 recognizes the change in impedance around the minimum impedance position (ko, jo), and reads out dictionary data DC that has been recorded in the EEPROM 35 in advance.

Figure 19:
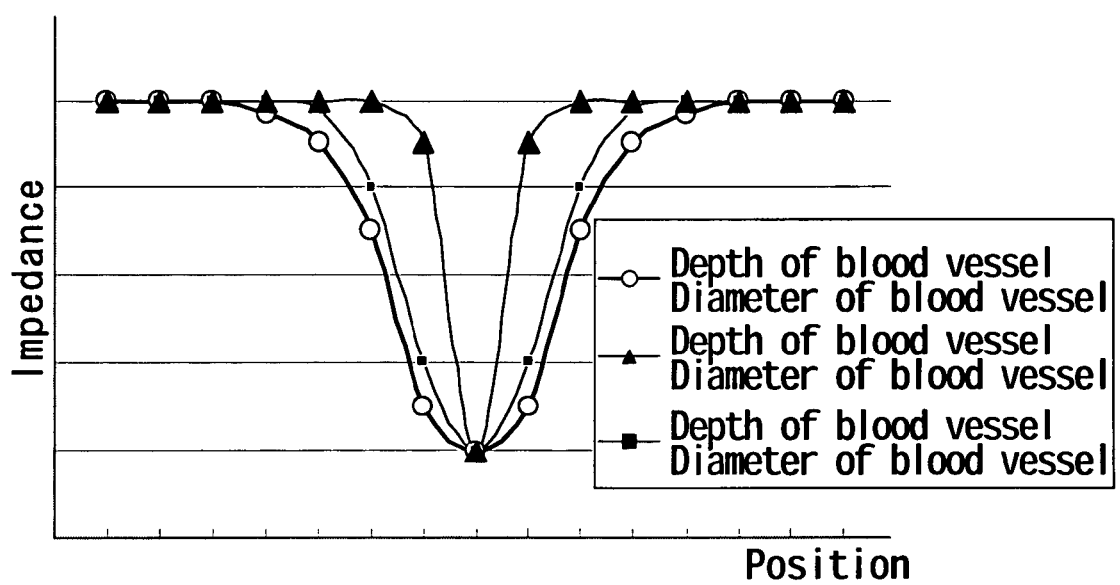
FIG. 19 shows a graphical representation indicative of the contents of dictionary data.

As shown in FIG. 19, this dictionary data DC is data that represents the change in impedance around the reference position (k, j), and the depth of blood vessel and diameter of blood vessel in the living organism corresponding to the change. In FIG. 18 and FIG. 19, for the sake of convenience, the degree of change in impedance around the "j" direction from the reference position (k, j) and the distance from the reference position (k, j) are shown.

Based on the dictionary data DC, the CPU 31 determines the depth of blood vessel and diameter of blood vessel corresponding to the change in impedance which is recognized at this time.

In this way, with the distance from an electrode corresponding to the minimum impedance position (ko, jo) to an electrode around the electrode and the impedance value at the distance being the judgment reference, that is, with the distance between electrodes and the degree of change in impedance detected from the electrodes being the reference, the depth of blood vessel and diameter of blood vessel can be determined.

According to the detection device 1, since the impedance can be detected for the respective electrode units UT1 to UTn through the quasi-electrostatic fields of a frequency band in which the electrical characteristics of the various biomedical tissues are scattered, even if the electrical characteristics of the various biomedical tissues in the living organism are reflected on the impedance, the case in which a blood vessel exists in the quasi-electrostatic fields and the case in which no blood vessel exists therein can be accurately differentiated from the difference of the respective impedances detected from the respective electrode units UT1 to UTn.

Furthermore, since the frequency band in which the electrical characteristics of the various biomedical tissues are scattered is a low frequency band, and the intensity of the quasi-electrostatic field that is transmitted according to the signal of the low frequency band is superior as compared with those of the radiation field and induction field, the influence of the radiation field and induction field is not reflected on the impedance detected by the respective electrode units UT1 to UTn through the quasi-electrostatic fields, which can differentiate the existence or nonexistence of blood more accurately.

Furthermore, even if materials such as clothes lie between the surface of the living organism and the electrodes in the quasi-electrostatic fields, since the relative dielectric constant of the materials are low in general, the impedance of the living organism placed in the quasi-electrostatic fields can be detected without being influenced by the materials lying between the surface of the living organism and the electrodes.

According to the detection device 1, as shown in FIG. 18 and FIG. 19, since the width of blood vessel (diameter of blood vessel) and depth of blood vessel are determined with the distance between the electrodes and the degree of change in impedance detected from the electrodes being the reference, much information concerning blood can be non-invasively and accurately obtained. Accordingly, when the diameter of blood vessel and depth of blood vessel are generated as biometric identification data, it becomes possible to prevent lowering of accuracy in discriminating whether or not an examined person is the identical person (False Rejection Rate (FRR), False Acceptance Rate (FAR)) based on the biometric identification data.

(4-5) Operation and Effect

In the above-described configuration, in the detection device 1, the core electrode Ea and the electrode Eb enclosing the core electrode Ea are enclosed by the conductive frame FM excluding the electric field irradiation direction (refer to FIG. 7B), and the first signal is output to the electrode Ea. On the other hand, to the electrode Eb, the second signal that has its waveform selected (refer to FIG. 8) on the basis of the first signal is output so that, when the quasi-electrostatic fields are generated from the paired electrodes Ea and Eb, the potential of the conductive frame FM is made constant not spatially but temporally.

Accordingly, in the detection device 1, the electrode Eb comes to be provided with the function of suppressing the oscillation of the conductive frame FM due to the quasi-electrostatic field generated by the electrode Ea to which the first signal is output. That is, the electrode Eb functions as a control electrode that controls the quasi-electrostatic fields generated from the paired electrodes Ea, Eb.

That is, in the detection device 1, the electric charge, which is to be obtained from the ground in case the conductive frame FM is completely grounded, can be obtained from the electrode Eb. Accordingly, even if the living organism is so arranged as to come into contact with the opening side of the conductive frame FM, the quasi-electrostatic field generated from the electrodes Ea comes to negate the quasi-electrostatic field generated from the electrode Eb before getting to the conductive frame FM. As a result, the quasi-electrostatic fields do not leak to the outside of the conductive frame FM due to the oscillation thereof, and, through the opening surface of the conductive frame FM, the electric fields are applied to the opening direction thereof (refer to FIG. 11).

Accordingly, in the detection device 1, the influence from the outside of the conductive frame FM with respect to the quasi-electrostatic fields can be reduced, and the quasi-electrostatic fields can be narrowed down to the electric field application subject, which makes it possible to accurately detect whether or not a colloid exists in the inside of the living organism according to the difference of impedances.

In the above-described configuration, by making the one electrode Eb of the paired electrodes Ea, Eb function as a control electrode, the influence from the outside of the conductive frame FM with respect to the quasi-electrostatic fields can be reduced, and since the quasi-electrostatic fields are narrowed down to the opening side to which the electric field application subject is arranged, it becomes possible to realize the detection device 1 of high detection accuracy.

(5) Other Embodiments

In the above-described embodiment, as a pair of electrodes, the disciform electrode Ea and the ringlike electrode Eb are employed, to which the present invention is not restricted, and electrodes of various shapes can be employed. The shapes of a pair of electrodes may be equal to each other, or may be different from each other.

Furthermore, as the positional relationship of a pair of electrodes, in the above-described embodiment, the electrode Ea and the electrode Eb that has its center made to accord with the electrode Ea and symmetrically encloses the electrode Ea are arranged on the same plane. That is, the paired electrodes Ea and Eb are concentrically arranged on a surface perpendicular to the electric field irradiation direction. On the other hand, the paired electrodes do not have to be concentrically arranged necessarily, and the paired electrodes may be arranged adjacently.

Moreover, the first electrode and second electrode of the paired electrodes may be arranged on planes different from each other. Instead of arranging the paired electrodes such that the electrodes are in contact with the surface of the opening OP of the conductive frame FM, the paired electrodes may be arranged in the space enclosed by the conductive frame FM.

For example, the second electrode may be so arranged as to symmetrically enclose the first electrode with an axis which passes through the first electrode and is parallel with the electric field irradiation direction (direction perpendicular to the opening surface of the opening OP) being the symmetry axis.

That is, a pair of electrodes should be arranged such that an electric dipole or an electric multipole is formed by the paired electrodes. One or both of the paired electrodes may be the electric dipole or electric multipole.

In this way, as the positional relationship of the first electrode and second electrode, and as the positional relationship of the first and second electrodes with respect to the frame, various configurations may be employed.

When the symmetric configuration is employed as the positional relationship of the first electrode and second electrode, and as the positional relationship of the first and second electrodes with respect to the frame, as compared with the case of not employing the symmetric configuration, since the entire uniformity of the paired electrodes and the conductive frame is improved, the first signal to be output to one electrode and the second signal to be output to the other electrode can have their waveforms made approximately equal to each other. As a result, with comparative ease, the waveform of the second signal can be selected on the basis of the first signal such that the potential of the conductive frame is made constant when electric fields are generated from the paired electrodes.

Furthermore, in the above-described embodiment, as a frame, there is employed the conductive frame FM that symmetrically encloses the entire circumference of the electrodes Ea and Eb with the electrode Ea being the center excluding the opening OP being the electric field irradiation part, to which the present invention is not restricted. For example, the entire circumference of the electrodes Ea and Eb excluding the opening OP being the electric field irradiation part does not have to be enclosed by setting the side wall of the conductive frame FM in the form of fences.

Figure 20A:
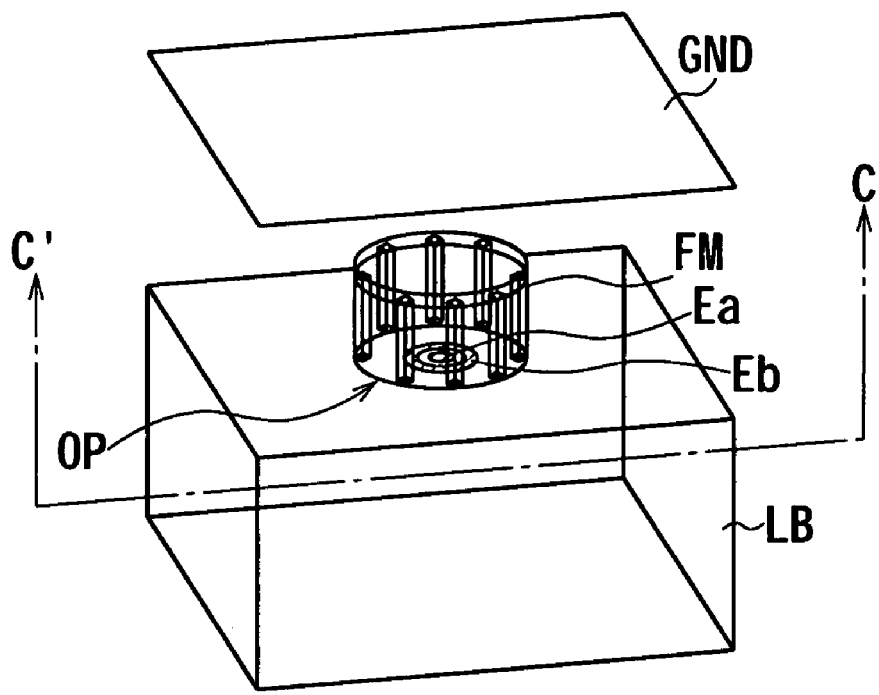
FIGS. 20A to 20C show schematic views of a model of the fourth simulation.
Figures 20B, 20C:
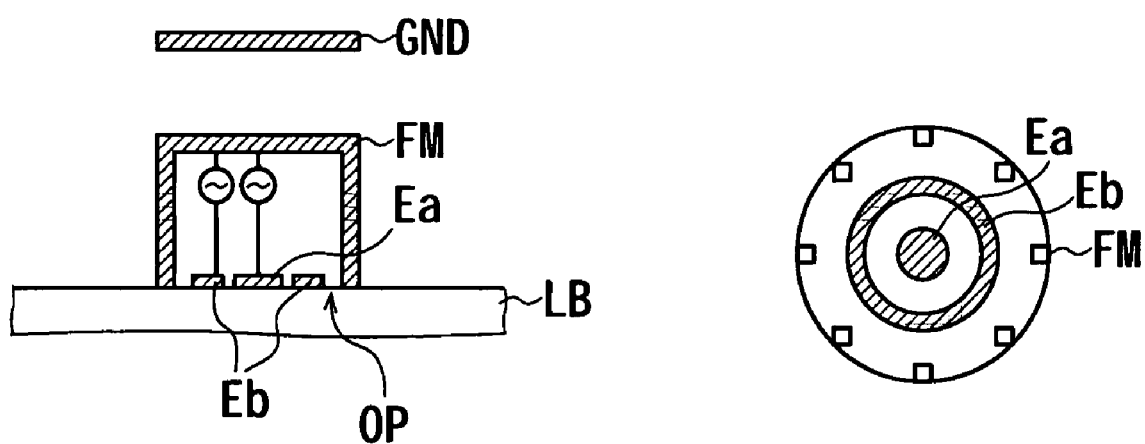
Figure 21:
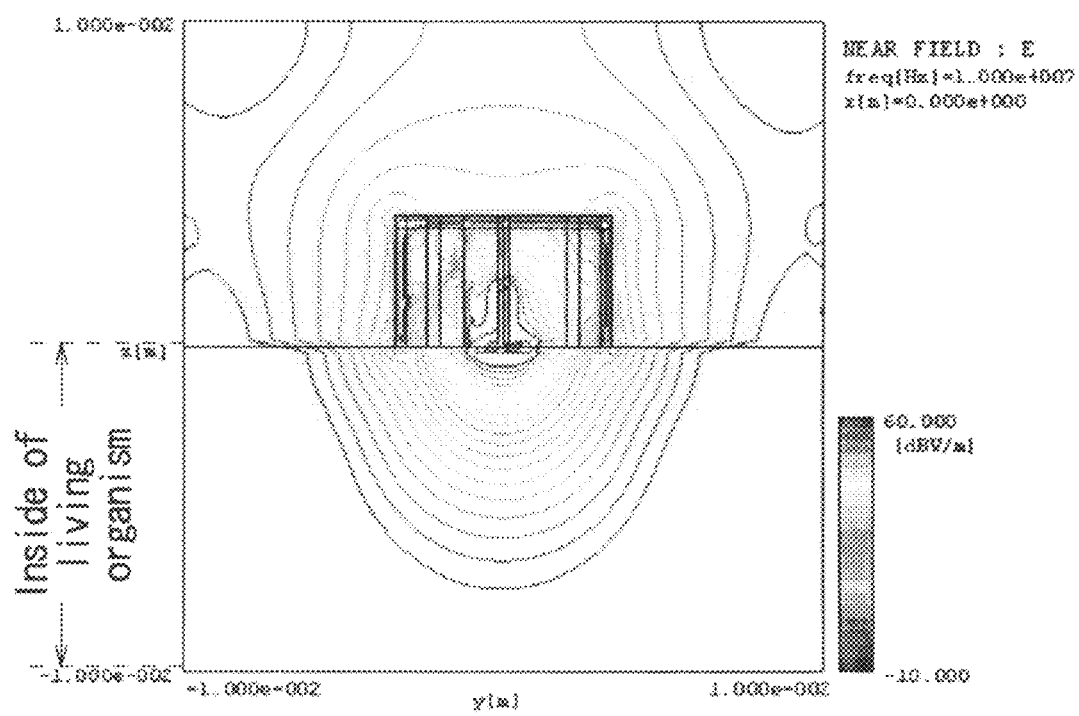
FIG. 21 shows a view indicative of an electric field intensity distribution pattern (Eb=0.12 V) by the fourth simulation.
Figure 22:
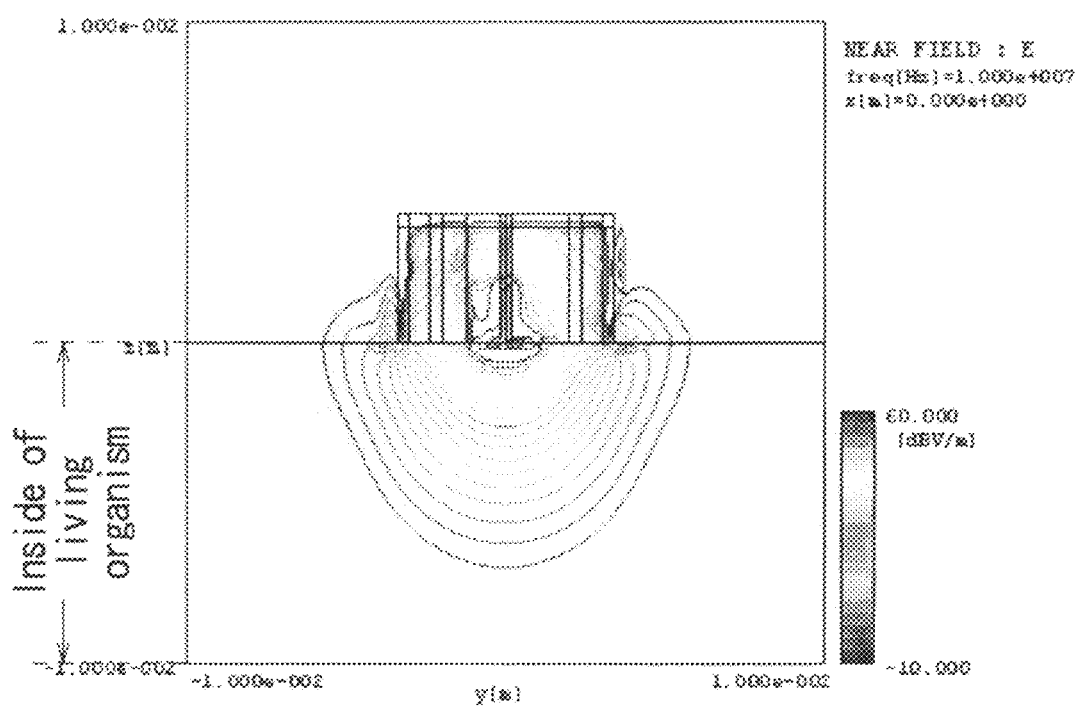
FIG. 22 shows a view indicative of an electric field intensity distribution pattern (Eb=0.15 V) by the fourth simulation.
Figure 23:
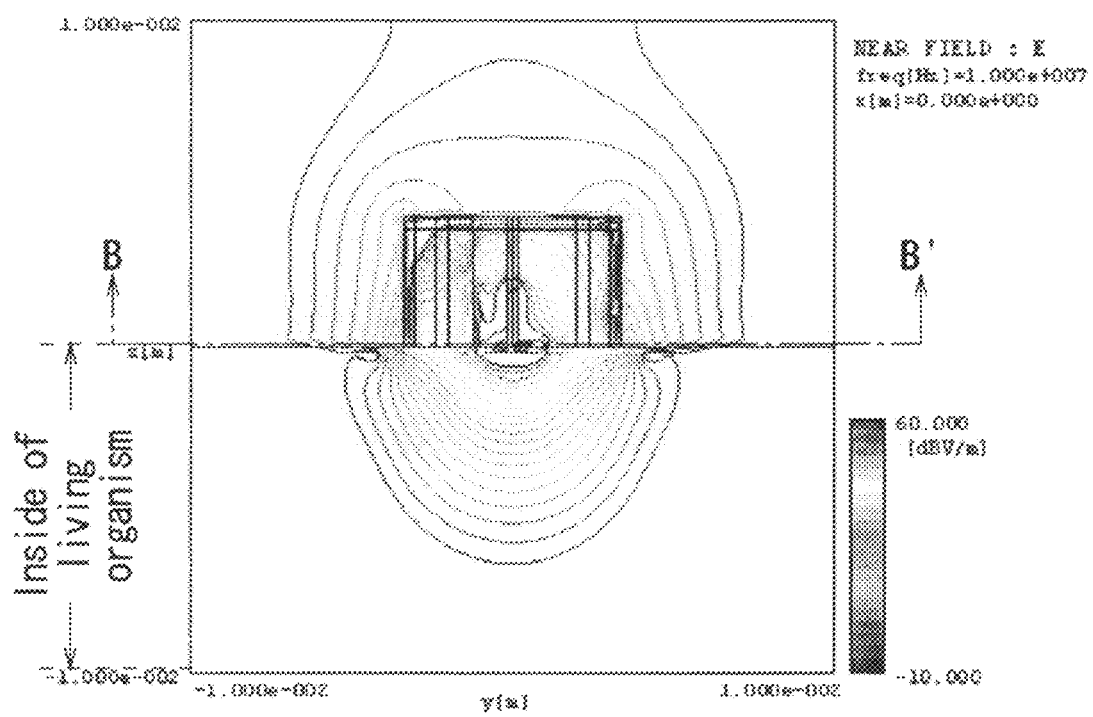
FIG. 23 shows a view indicative of an electric field intensity distribution pattern (Eb=0.17 V) by the fourth simulation.
Figure 24:
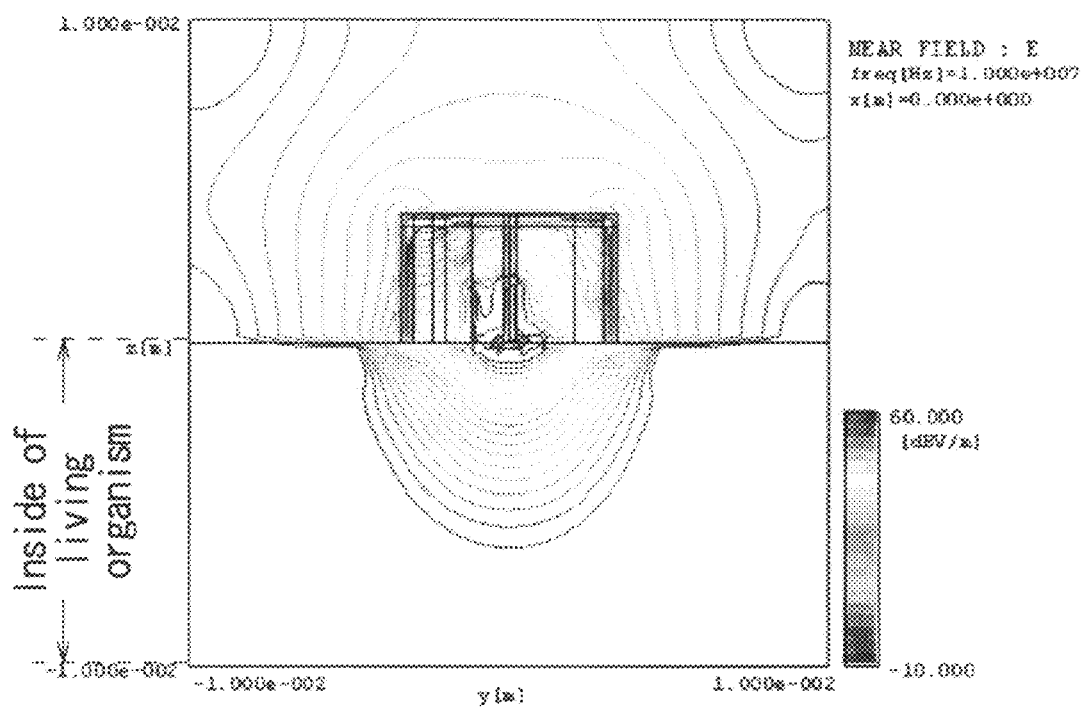
FIG. 24 shows a view indicative of an electric field intensity distribution pattern (Eb=0.20 V) by the fourth simulation.

FIGS. 20A to 20C show models of the simulation (referred to as fourth simulation, hereinafter) in case the side wall of the conductive frame FM is set in the form of fences, and FIG. 21 to FIG. 25 show electric field distribution patterns indicative of parts of the result (parts corresponding to the third simulation) obtained by simulating the fourth simulation model under the condition similar to that under which the third simulation is performed. The electric field distribution patterns shown in FIG. 21 to FIG. 25 are appended as reference FIG. 7A to reference FIG. 11.

As is clear from FIG. 21 to FIG. 25, in this fourth simulation, when the amplitude of a signal to be applied to the core electrode Ea is 1 V, and the amplitude of a signal to be applied to the electrode Eb enclosing the core electrode Ea is 0.15 V, the quasi-electrostatic fields do not spread not only to the outside of the conductive frame FM but also around the vicinity of the surface of the living organism.

Figure 25:
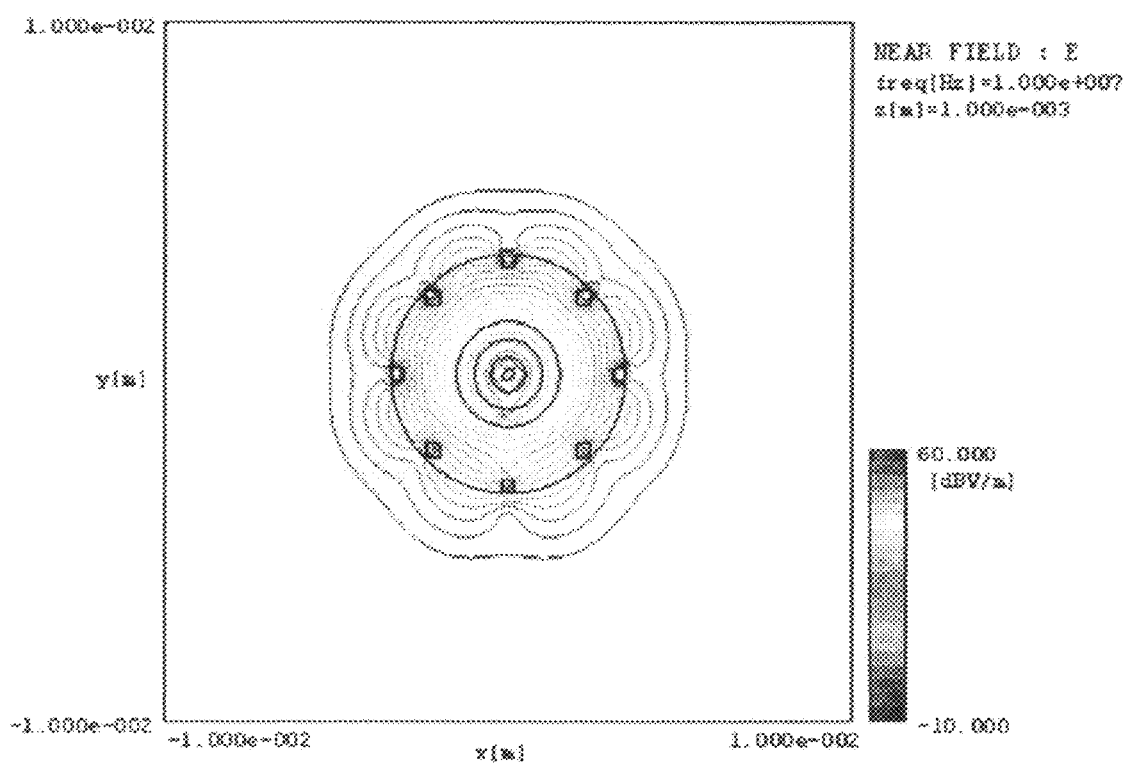
FIG. 25 shows a view indicative of an electric field intensity distribution pattern at B-B' cross-section shown in FIG. 23.

In the fourth simulation, even if the electric fields do not leak to the outside of the conductive frame FM due to the oscillation thereof, since the side wall of the conductive frame FM is set in the form of fences, the electric fields leak to the outside of the conductive frame FM through the clearances between the fences (refer to especially FIG. 25). On the other hand, since the quasi-electrostatic fields do not leak at the upper part of the conductive frame FM, as compared with the conventional case in which a frame is arranged only around an electrode (FIG. 5), the influence from the outside of the conductive frame FM with respect to the quasi-electrostatic fields can be reduced, and the quasi-electrostatic fields can be narrowed down to the electric field application subject.

Furthermore, the frame is not restricted to the case in which the side wall of the conductive frame FM is set in the form of fences. As the shape of the frame, there may be employed the spherical shape, cylindrical shape, conical shape, truncated cone shape, or other arbitrary solid shapes so long as the electric field irradiation direction is opened. The shape of the cross-section or the shape of the basal plane of the solid shape is not restricted to the circular shape, and there may be employed the quadrangular shape, hexagonal shape, asteroid shape, or other arbitrary solid shapes.

As the frame, there may be desirably employed a frame that encloses the entire circumference of the paired electrodes excluding the electric field irradiation part, especially, a frame in the form of a cylinder that is defined by the central axis of the electrodes which is perpendicular to a plane on which the electrodes are arranged, and has a basal plane attached to one end of the cylinder, and has its other end of the cylinder which is opposed to the one end of the cylinder opened. The reason is, since the uniformity can be easily secured as compared with the case of employing the complicated shape, with comparative ease, the waveform of the second signal can be selected on the basis of the first signal such that the potential of the conductive frame is made constant when electric fields are generated from the paired electrodes.

Figure 26:
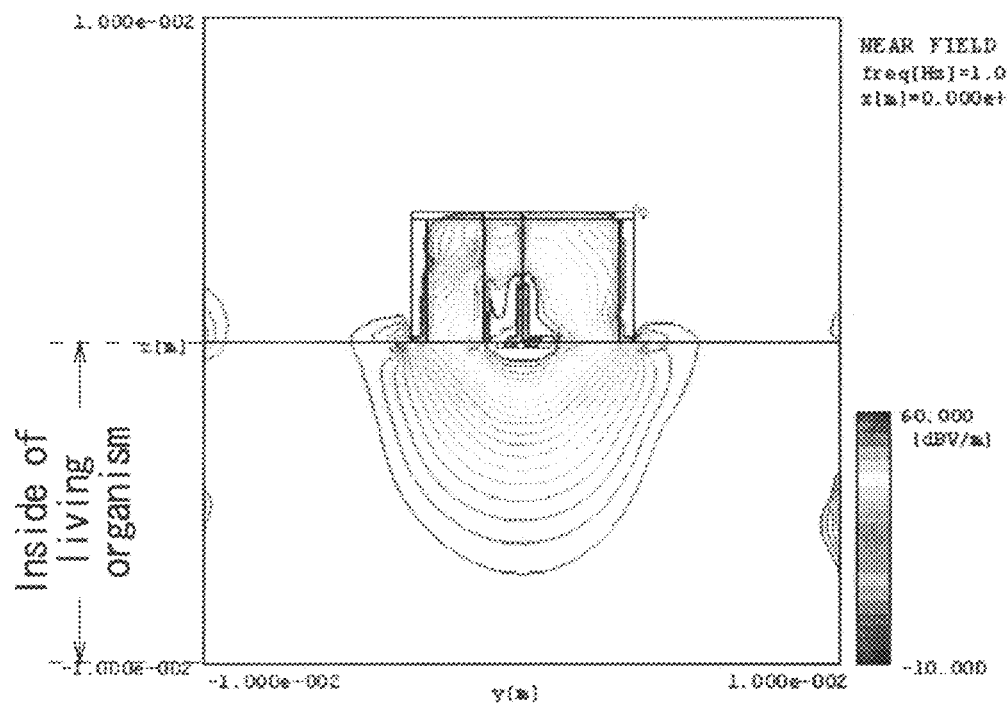
FIG. 26 shows a view indicative of an electric field intensity distribution pattern when $\in r=1800000$, while $\sigma=0$ S/m as the electrical characteristics of a frame.
Figure 27:
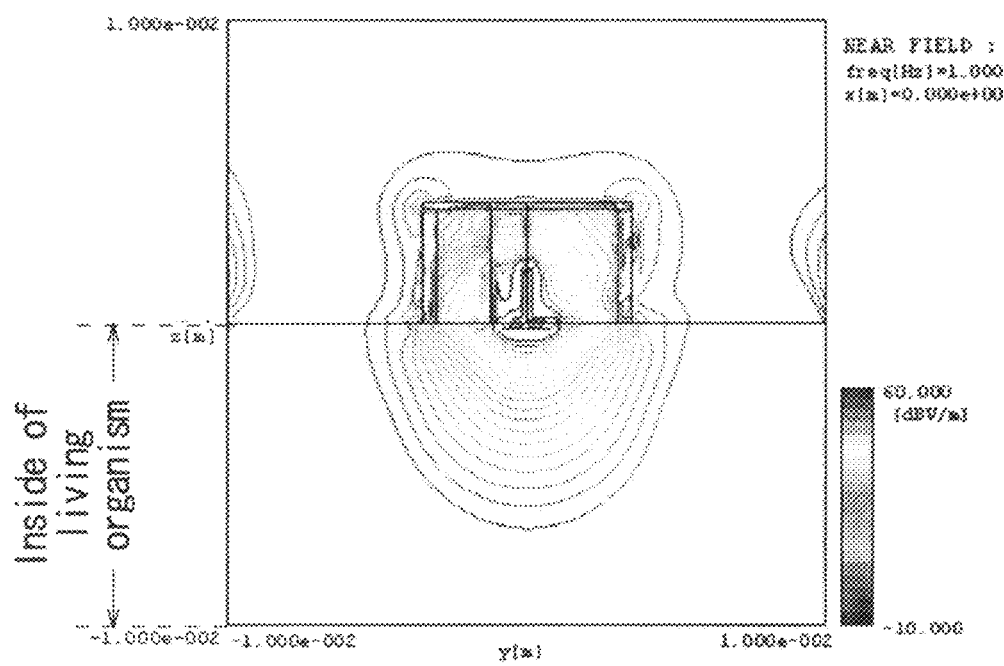
FIG. 27 shows a view indicative of an electric field intensity distribution pattern when $\in r=20000$, while $\sigma=0$ S/m as the electrical characteristics of a frame.

The frame is not restricted to a conductor. FIG. 26 shows an electric field distribution pattern by the simulation when the relative dielectric constant is 1800000, while the electrical conductivity is 0 S/m, as the electrical characteristics of the frame. Furthermore, FIG. 27 shows an electric field distribution pattern by the simulation when the relative dielectric constant is 20000, while the electrical conductivity is 0 S/m. The electric field distribution patterns shown in FIG. 26 and FIG. 27 are appended as reference FIG. 12 and reference FIG. 13.

As is clear from FIG. 25 and FIG. 26, when employing a dielectric having a significantly high dielectric constant, a result similar to that of a conductor can be obtained. Accordingly, the frame is not restricted to a conductor so long as the frame has a constant electrical conductivity.

Furthermore, in the above-described embodiment, as an output unit that outputs the first signal to one of the paired electrodes and outputs the second signal to the other of the paired electrodes, the signal output control unit 20 (FIG. 14) is employed, to which the present invention is not restricted, and other units may be widely employed.

Figure 28:
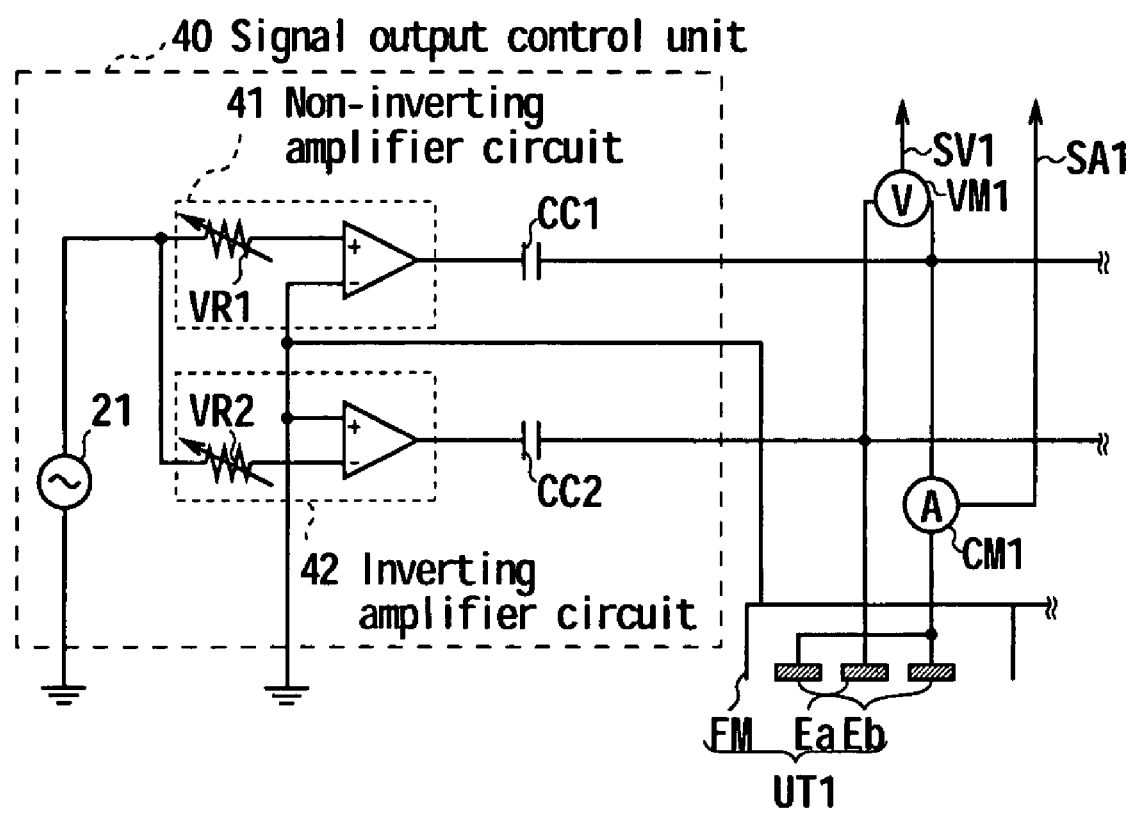
FIG. 28 shows a schematic view indicative of the configuration of a signal output control unit according to another embodiment.

For example, in the above-described embodiment, as a unit to generate the first signal output to the electrodes Ea and generate the second signal output to the electrodes Eb such that the phases thereof are made opposite to each other by 180°, the transformer 27 (FIG. 14) is employed. On the other hand, as indicated by a signal output control unit 40 shown in FIG. 28, there may be employed a non-inverting amplifier circuit 41 and an inverting amplifier circuit 42.

In the above-described embodiment, as a unit to adjust the amplitude ratio of the first signal and second signal, taps, not shown, are employed. On the other hand, in this case, in the signal output control unit 40 shown in FIG. 28, variable resistors VR1 and VR2 of the non-inverting amplifier circuit 41 and inverting amplifier circuit 42 work as a unit to adjust the amplitude ratio, respectively. When thus configured signal output control unit 40 is employed, effects similar to those in the above-described embodiment can be obtained.

As for the first signal and second signal, signals which have their phases made opposite to each other by 180° and have their amplitude ratio set to a predetermined value are generated in the signal output control unit 20 and in the signal output control unit 40. On the other hand, instead, signals which have the same amplitude and have their phases shifted with respect to each other by a predetermined angle may be employed. In this case, effects similar to those in above-described embodiment can be obtained.

Furthermore, there may be employed a signal output control unit that includes a signal generation source that outputs a first signal to the electrode Ea, and a signal generation source that outputs a second signal to the electrode Eb which has its waveform selected on the basis of the first signal such that the potential of the conductive frame FM is set constant when the electric fields are generated from the paired electrodes Ea, Eb. In this case, effects similar to those in the above-described embodiment can be obtained.

The present invention is not restricted to these examples, and, instead of the signal output control unit 20, units of other configurations may be widely employed.

In the above-described embodiment, the impedance of a living organism is detected using the quasi-electrostatic field, to which the present invention is not restricted, and the present invention can be employed in the case of communicating data in a specific range using the induction field and quasi-electrostatic field.

In this case, influence of interference waves from the outside of the conductive frame FM with respect to the electric field of the communication subject can be reduced, and the electric field of the communication subject can be narrowed down to reception electrodes, which can improve communication efficiency.

In the above-described embodiment, the case of detecting whether or not blood exists is described, to which the present invention is not restricted, and various colloids in the inside of a living organism such as sol or bone marrow fluid, cerebrospinal fluid, lymph fluid, and gas or flatus, pulmonary gas can be detected. In this case, when the arrangement position of the electrodes and the frequency of the signals to be applied to the electrodes are arbitrarily changed according to the kind of the colloid, similar to the case of the above-described embodiment, it becomes possible to detect whether or not a targeted colloid exists.

In the above-described embodiment, the case of determining the width of blood vessel (diameter of blood vessel) containing blood and the depth of blood (blood vessel) in the inside of a living organism is described, to which the present invention is not restricted, and the width and depth of the bone marrow tissue containing bone marrow fluid, the width and depth of the cerebrospinal tissue containing cerebrospinal fluid, the width and depth of a lymphatic vessel containing lymph fluid, the width and depth of the large intestine tissue containing flatus, the width and depth of the lung tissue containing pulmonary gas, and tomographic images of various tissues can be determined.

In the above-described embodiment, the ratio of the blood cell component and the blood serum component in blood (blood viscosity) is determined, to which the present invention is not restricted, and the ratio of the sphere component and the solution component in bone marrow fluid, cerebrospinal fluid, and lymph fluid, and the ratio of the particle component and the solvent component in flatus and pulmonary gas may be determined.

The present invention can be employed in discriminating a living organism and in judging the state of a living organism.

It should be understood by those skilled in the art that various modifications, combinations sub-combinations and alterations may occur depending on design requirements and other factors insofar as they are within the scope of the appended claims or the equivalents thereof.

What is claimed is:

1. An electric field control device that applies electric fields to an electric field application subject, including:
   a first electrode and a second electrode that generate the electric fields;
   a frame that is arranged around the first electrode and second electrode, and is connected to the first electrode and second electrode, the first electrode, the second electrode, and the frame forming an electrode unit, wherein the frame is so arranged as to symmetrically enclose the first electrode with the first electrode being the center, wherein the frame is set in the form of fences with clearances between the fences;
   an opening that is formed at one end of the frame;
   output means for outputting a first signal to the first electrode, and outputting a second signal to the second electrode,
      wherein, when the electric fields are generated from the first electrode and second electrode, the output means outputs the second signal to the second electrode so that the potential of the frame is not changed temporally and made constant; and
   a detection unit for detecting an impedance for the electrode unit through a quasi-electrostatic field.

2. The electric field control device according to claim 1, wherein the output means comprises:
   generation means for generating the first signal, and generating the second signal that has its phase set opposite with respect to the first signal; and
   adjustment means for adjusting the amplitude ratio of the first signal and second signal.

3. The electric field control device according to claim 1, wherein the output means outputs the first signal and the second signal by setting frequencies thereof so that, in the electric fields formed at the outside of the opening, the intensity of the quasi-electrostatic fields is superior as compared with that of the induction fields at a predetermined distance.

4. The electric field control device according to claim 1, wherein the frame encloses the entire circumference of the first electrode and second electrode excluding the opening.

5. The electric field control device according to claim 1, wherein the second electrode is so arranged as to symmetrically enclose the first electrode with an axis which passes through the first electrode and is parallel with the electric field irradiation direction being the symmetry axis.

6. The electric field control device according to claim 1, wherein
   the first electrode and second electrode are arranged on the same plane,
   the frame is in the form of a cylinder that is defined by the central axis of the first electrode which passes through the first electrode and is perpendicular to the plane on which the first electrode and second electrode are arranged, and has a basal plane attached to one end of the cylinder, and
   the opening corresponds to the other basal plane which is opposed to the basal plane attached to the one end of the cylinder configuring the frame.

7. The electric field control device according to claim 1, wherein the first electrode and second electrode are so placed as to be substantially in contact with the surface of the opening.

8. The electric field control device according to claim 1, wherein the first electrode is an electric dipole or an electric multipole.

9. The electric field control device according to claim 1, wherein the first electrode and second electrode are placed so that an electric dipole or an electric multipole are formed by the first electrode and second electrode.

10. The electric field control device according to claim 1, wherein the frame is made of conductive material.

11. An electric field control device that applies electric fields to an electric field application subject, including:
    a plurality of electrode units arranged in a lattice shaped pattern, each electrode unit including:
       a first electrode and a second electrode that generate the electric fields;
       a frame that is arranged around the first electrode and second electrode, and is connected to the first electrode and second electrode; and
       an opening that is formed at one end of the frame;
    an output unit that outputs a first signal to each first electrode, and outputs a second signal to each second electrode,
       wherein, when the electric fields are generated from each first electrode and second electrode, the output unit outputs the second signal to each second electrode so that the potential of each frame is not changed temporally and made constant,
       wherein the output unit is configured to output the first and second signals sequentially to each of the electrode units to prevent the detection unit from detecting impedances due to the mutual interaction among quasi-electrostatic fields; and
    a detection unit for detecting an impedance for each electrode unit through a quasi-electrostatic field.

12. A detection device that detects a predetermined detection subject in a living organism, including:
    a plurality of electrode units arranged in a lattice shaped pattern, each electrode unit including:
       a first electrode and a second electrode, the second electrode having a ring shape enclosing an entire circumference of the first electrode;
       a frame that is arranged around the first electrode and second electrode, and is connected to the first electrode and second electrode;
       an opening that is formed at one end of the frame;
    an output unit that outputs a first signal and a second signal to each first electrode and each second electrode by setting frequencies thereof so that, in the electric fields formed through the opening by each first electrode and each second electrode, the intensity of the quasi-electrostatic fields is superior as compared with that of the induction fields at a predetermined distance;
    an impedance detection unit that detects the impedance of the living organism placed in the electric fields from each first electrode and each second electrode using the quasi-electrostatic field; and
    a colloid detection unit for detecting whether or not a colloid exists in the inside of the living organism according to the difference of the respective detected impedances,
    wherein, when the electric fields are generated from each first electrode and each second electrode, the output unit outputs the second signal to each second electrode so that the potential of each frame is not changed temporally and made constant,
    wherein the output unit is configured to output the first and second signals sequentially to each of the electrode units to prevent the detection unit from detecting impedances due to the mutual interaction among quasi-electrostatic fields.

13. An electric field control device that applies electric fields to an electric field application subject, comprising:

a plurality of electrode units arranged in a lattice shaped pattern, each electrode unit including:

a first electrode and a second electrode that generate the electric fields;

a frame that is arranged around the first electrode and second electrode, and is connected to the first electrode and second electrode; and an opening that is formed at one end of the frame;

an output unit that outputs a first signal to each first electrode, and outputs a second signal to each second electrode, wherein, when the electric fields are generated from each first electrode and second electrode, the output unit outputs the second signal to each second electrode so that the potential of each frame is not changed temporally and made constant; and a detection unit for detecting an impedance for each electrode unit through a quasi-electrostatic field, wherein the detection unit further includes a calculation unit for calculating impedance values corresponding to each of the electrode units.

14. The electric field control device according to claim 13, wherein the detection unit further includes a central processing unit for storing impedance values from the calculation unit, the central processing unit configured to replace the impedance values into a matrix corresponding to an arrangement of the electrode units.

15. The electric field control device according to claim 14, wherein the central processing unit is further configured to detect a minimum impedance for each electrode unit and determine a minimum impedance position representing a center of a cross-section surface of a blood vessel in a blood flow direction.

16. The electric field control device according to claim 15, further including an EEPROM including dictionary data representing a change in impedance around a reference position and a depth and diameter of a blood vessel in a living organism corresponding to the change.

17. The electric field control device according to claim 16, wherein the central processing unit is configured to determine a depth and diameter of a blood vessel in the electric field application subject based on the dictionary data.

* * * * *